United States Patent
Cutler

(10) Patent No.: US 12,428,643 B2
(45) Date of Patent: Sep. 30, 2025

(54) TREATING HERPESVIRUS-MEDIATED INTESTINAL DYSFUNCTION FOR PREVENTION OF AGE-RELATED NEURODEGENERATION

(71) Applicant: Battle Biotech, LLC, Ann Arbor, MI (US)

(72) Inventor: Richelle Gayle Cutler, Ann Arbor, MI (US)

(73) Assignee: Battle Biotech L.L.C., Ypsilanti, MI (US)

( * ) Notice: Subject to any disclaimer, the term of this patent is extended or adjusted under 35 U.S.C. 154(b) by 529 days.

(21) Appl. No.: 16/709,607

(22) Filed: Dec. 10, 2019

(65) Prior Publication Data
US 2021/0171952 A1 Jun. 10, 2021

(51) Int. Cl.
*C12N 15/113* (2010.01)
*A61K 9/00* (2006.01)
*C12N 1/20* (2006.01)
*A61K 45/06* (2006.01)

(52) U.S. Cl.
CPC ............ *C12N 15/1133* (2013.01); *C12N 1/20* (2013.01); *A61K 9/0053* (2013.01); *A61K 45/06* (2013.01); *C12N 2310/122* (2013.01); *C12N 2310/141* (2013.01)

(58) Field of Classification Search
CPC .......... C12N 15/1133; C12N 2310/141; A61K 9/0053; A61K 9/5068
See application file for complete search history.

(56) References Cited

PUBLICATIONS

Abend et al (J. Virol. 86(21):11663-11674, 2012) (Year: 2012).*
Blenkiron et al (PLoS One 11(8):e0160440, 16 pages, 2016) (Year: 2016).*
Valderrama et al. (In Lipid Nanocarriers for Drug Targeting (2018) pp. 199-299) (Year: 2018).*
Fantappie et al. (Journal of Extracellular Vesicles 2014, 3: 24015) (Year: 2014).*
Liu et al. (Front. Microbiol. 9:1502, 8 pages, 2018) (Year: 2018).*
Woodhall et al. (J. Biol. Chem 281(49): 37652-37660, 2006) (Year: 2006).*
Merkl et al. (J. Virol. 92(10): e00057-18, 19 pages, 2018) (Year: 2018).*
Sultanova et al. (Clinical Microbiology and Infection 23: 50.e1e50.e5, 2017) (Year: 2017).*
Halenius et al. (Hindawi 2014: 472978, 15 pages, 2015) (Year: 2015).*
Harley et al (Nature Genetics 50:699-707, 2018) (Year: 2018).*
Gomez et al. (Front. Genet. 9:92, 11 pages, 2018) (Year: 2018).*
Van Herwijnen et al. (Front. Nutr. 5:81, 6 pages, 2018) (Year: 2018).*
Lerner et al (Front. Microbiol. 8:1392, 2017) (Year: 2017).*
Posnett et al (Arth Res Ther 7(2):74-84, 2005) (Year: 2005).*
Dreyfus et al (Autoimmunity Reviews 11 (2011) 88-97) (Year: 2011).*
Tsatsaronis (Trends in Microbiology, May 2018, vol. 26, No. 5: 401-410) (Year: 2018).*
Alvarez-Erviti (Nature Biotech. 29(4):341-347, 2011) (Year: 2011).*
Kojima et al (Nature Comm 9:1305, (2018) (Year: 2018).*
Yuan et al (Biomaterials 142 (2017) 1-12) (Year: 2017).*
Bannerjee et al (Nanoscale, 2019, 11, 13243) (Year: 2019).*
Hwang et al (Nature Scientific Reports 5:15636, 2015, 10 pages) (Year: 2015).*
Koeppen et al (PLoS Pathog 12(6): e1005672) (Year: 2016).*
Xiang et al (Nature Biotechnology 24(6): 697-702) (Year: 2006).*
Hong et al ( Int. J. Mol. Sci. 2022, 23, 2769) (Year: 2022).*
Yan et al (Cell Cycle, 18:22, 3072-3084, 2019) (Year: 2019).*
Godshalk et al (Cell Cycle, 7:22, 3595-3600,2008) (Year: 2008).*
Choi et al (Int. J. Mol. Sci. 2015, 16, 7413-7427) (Year: 2015).*
Li et al (Experimental and Therapeutic Medicine 7: 1291-1296, 2014) (Year: 2014).*
Tsai et al (Journal of Virology, Jan. 2009, p. 622-632) (Year: 2009).*
SP100 UniProt variant page downloaded from https://www.uniprot.org/uniprotkb/P23497/variant-viewer (Year: 2024).*
Zhang et al., Exosome-Induced Regulation in Inflammatory Bowel Disease. Frontiers in Immunology, pp. 1-9; vol. 10, (1464) Jun. 28, 2019.
Zhang et al., Exosomes in Pathogen Infections: A Bridge to Deliver Molecules and Link Functions, Frontiers in Immunology, pp. 1-11; vol. 9, (90) Feb. 12, 2018.
Manca et al., Milk Exosomes are Bioavailable and Distinct MicroRNA Cargos have Unique Tissue Distribution Patterns, Scientific Reports, pp. 1-11; vol. 8 (11321) Jul. 22, 2018.
Aqill et al., Milk Exosomes—Natural Nanoparticles for siRNA Delivery, Caner Lett., pp. 186-195; 449, May 1, 2019.
Munagala et al., Bovine Milk-derived Exosomes for Drug Delivery, Cancer Lett. pp. 48-61; 371(1) Feb. 1, 2016.
Mendt et al., Generation of Testing of Clinical-grade Exosomes for Pancreatic Cancer, JCI Insight, e99263; 3(8) Apr. 19, 2018.
Gangadaran et al., An Update on in Vivo Imaging of Extracellular Vesicles as Drug Delivery Vehicles. Front Pharmacol. pgs. 1-14; 9(169) Feb. 28, 2018.
Sun et al., Cytoprotective Effects of Galacto-oligosaccharides on Colon Epithelial Cell Via Up-regulation MiR-19b, pp. 1-7, Life Sciences; 231 (116589), Jun. 19, 2019.

(Continued)

*Primary Examiner* — Richard A Schnizer
(74) *Attorney, Agent, or Firm* — Richelle G. Cutler

(57) ABSTRACT

Human herpesviruses can infect barrier and immune cells of the intestines to cause microbiome dysbiosis and inflammation. Microbiome dysbiosis can affect the brain function, and inflammation can compromise the intestinal barrier and lead to microbial translocation. Embodiments may restrict herpesvirus activity and injury by 1) the oral administration of exosomes containing factors to inhibit viral activity and restore homeostasis, and 2) the oral administration of recombinant bacteria that produce exosomes containing factors to inhibit viral activity and restore homeostasis. Embodiments also measure HHV activity in stool by ELISA immunoassay of HHV proteins.

17 Claims, No Drawings
Specification includes a Sequence Listing.

(56) References Cited

PUBLICATIONS

Okahara et al., Colonic Cytomegalovirus Detection by Mucosal PCR and Antiviral Therapy in Ulcerative Colitis, PLoS One pp. 1-11; 12(9) e0183951, Sep. 8, 2017.

Ding et al., lncRNA Mirt2 Is Downregulated in Ulcerative Colitis and Regulates IL-22 Expression and Apoptosis in Colonic Epithelial Cells, Gastroenterology Research and Practice, pp. 1-5; (8154692), Oct. 2019.

Oszvald et al., Extracellular Vesicles Transmit Epithelial Growth Factor Activity in the Intestinal Stem Cell Niche, Stem Cells, pp. 291-300; 38 (2), Nov. 1, 2019.

Clairembault et al., Structural Alterations of the Intestinal Epithelium Barrier in Parkinson's Disease, Acta Neuropathologica Communications, pp. 1-9; 3(12), Mar. 15, 2015.

Bentz et al., Human Cytomegalovirus (HCMV) Infection of Endothelial Cells Promotes Naïve Monocyte Extravasation and Transfer of Productive Virus To Enhance Hematogenous Dissemination of HCMV, J. Virol. pp. 11539-11555; 80 (23), Dec. 2006.

Kowalski K. and Mulak A. Brain-Gut-Microbiota Axis in Alzheimer's Disease, J. Neurogastroenterol Motil, pp. 48-60; 25 (1), Jan. 2019.

Abate et al., Major Human Cytomegalovirus Structural Protein pp65 (ppUL83) Prevents Interferon Response Factor 3 Activation in the Interferon Response, J. Virol. pp. 10995-11006; 78 (20), Sep. 27, 2004.

Dai et al., The Smallest Capsid Protein Mediates Binding of the Essential Tegument Protein pp150 to Stabilize DNA-Containing Capsids in Human Cytomegalovirus, PLoS Pathogens e1003525; 9 (8) Aug. 2013.

Fu et al., MicroRNA miR-21 Attenuates Human Cytomegalovirus Replication in Neural Cells by Targeting Cdc25a, J. Virol. pp. 1070-1082; 89 (2), 2015.

Sharma et al., Efficient Sleeping Beauty DNA Transposition from DNA Minicircles, Molecular Therapy—Nucleic Acids pp. 1-10; 2 (e74), 2013.

Monleo'n et al., Plasma metabolomics profiling for the prediction of cytomegalovirus DNAemia and analysis of virus-host interaction in allogeneic stem cell transplant recipients,Journal of General Virology (2015), 96, 3373-3381.

Goodgame, R.W., Viral Infections of the Gastrointestinal Tract, Current Gastroenterology Reports 1999, 1:292-300.

Kumar et al., MicroRNA hsa-miR-324-5p Suppresses H5N1 Virus Replication by Targeting the Viral PB1 and Host CUEDC2, J. Virol. Oct. 2018 vol. 92 Issue 19, 1-17.

Fan et al., MiR-185-5p suppresses HBV gene expression by targeting ELK1 in hepatoma carcinoma cells, Life Sci. Nov. 15, 2018;213:9-17. doi: 10.1016/j.lfs.2018.10.016. Epub Oct. 9, 2018.

Kew et al., HCMV activation of ERK-MAPK drives a multifactorial response promoting the survival of infected myeloid progenitors, J Mol Biochem. 2017;6(1):13-25.

Johnson et al., Human Cytomegalovirus Up-Regulates the Phosphatidylinositol 3-Kinase (PI3-K) Pathway, J. Virol. Jul. 2001, vol. 75, No. 13, 6022-6032.

Schwarzenbacher et al., MiR-1287-5p inhibits triple negative breast cancer growth by interaction with phosphoinositide 3-kinase CB, Breast Cancer Research(2019) 21:20.

Kobayashi et al., MiR-199a Inhibits Secondary envelopment of Herpes Simplex Virus-1, Scientific Reports | 7: 6650 | DOI:10.1038/s41598-017-06754-3, 2018.

Santhakumar et al., Combined agonist-antagonist genome-wide functional screening identifies broadly active antiviral microRNAs, PNAS, Aug. 3, 2010, vol. 107; No. 31, 13830-13835.

Aiello, Allison E.; Haan, Maryn; Blythe, Lynn; Moore, Kari; Gonzalez, Jeffrey M.; Jagust, William, The influence of latent viral infection on rate of cognitive decline over 4 years (2006) Journal of the American Geriatrics Society, 54 (7) : 1046-1054.

Scheper, W.; Hoozemans, J. J. M .; Hoogenraad, C. C.; Rozemuller, A. J. M.; Eikelenboom, P.; Baas, F. (2007): Rab6 is increased in Alzheimer's disease brain and correlates with endoplasmic reticulum stress. In Neuropathol Appl Neurobiol 33 (5), pp. 523-532. DOI: 10.1111/j.1365-2990.2007.00846.x.

Schlager, Max A.; Kapitein, Lukas C.; Grigoriev, Ilya; Burzynski, Grzegorz M.; Wulf, Phebe S.; Keijzer, Nanda et al. (2010): Pericentrosomal targeting of Rab6 secretory vesicles by Bicaudal-D-related protein 1 (BICDR-1) regulates neuritogenesis. In The EMBO journal 29 (10), pp. 1637-1651. DOI: 10.1038/emboj.2010.51.

Schreiner, Sabrina; Wodrich, Harald (2013): Virion factors that target Daxx to overcome intrinsic immunity. In J Virol 87 (19), pp. 10412-10422. DOI: 10.1128/JVI.00425-13.

Shen, Xue-Ning; Niu, Li-Dong; Wang, Yan-Jiang; Cao, Xi-Peng; Liu, Qiang; Tan, Lan et al. (2019): Inflammatory markers in Alzheimer's disease and mild cognitive impairment. A meta-analysis and systematic review of 170 studies. In Journal of neurology, neurosurgery, and psychiatry 90 (5), pp. 590-598. DOI: 10.1136/jnnp-2018-319148.

Sims, Rebecca; van der Lee, Sven J.; Naj, Adam C.; Bellenguez, Céline; Badarinarayan, Nandini; Jakobsdottir, Johanna et al. (2017): Rare coding variants in PLCG2, ABI3, and TREM2 implicate microglial-mediated innate immunity in Alzheimer's disease. In Nature genetics 49 (9), pp. 1373-1384. DOI: 10.1038/ng.3916.

Small, Scott A.; Simoes-Spassov, Sabrina; Mayeux, Richard; Petsko, Gregory A. (2017): Endosomal Traffic Jams Represent a Pathogenic Hub and Therapeutic Target in Alzheimer's Disease. In Trends in neurosciences 40 (10), pp. 592-602. DOI: 10.1016/j.tins.2017.08.003.

Song, Misun; Kwon, Young-Ah; Lee, Yujin; Kim, Hyeran; Yun, Ji Hea; Kim, Seonwoo; Kim, Doh Kwan (2012): G1/S cell cycle checkpoint defect in lymphocytes from patients with Alzheimer's disease. In Psychiatry investigation 9 (4), pp. 413-417. DOI: 10.4306/pi.2012.9.4.413.

Stampfer, M. J. (2006): Cardiovascular disease and Alzheimer's disease. Common links. In Journal of internal medicine 260 (3), pp. 211-223. DOI: 10.1111/j.1365-2796.2006.01687.x.

Tandon, Ritesh; Mocarski, Edward S. (2012): Viral and host control of cytomegalovirus maturation. In Trends in microbiology 20 (8), pp. 392-401. DOI: 10.1016/j.tim.2012.04.008.

Terenzio, Marco; Golding, Matthew; Russell, Matthew R. G.; Wicher, Krzysztof B.; Rosewell, Ian; Spencer-Dene, Bradley et al. (2014): Bicaudal-D1 regulates the intracellular sorting and signalling of neurotrophin receptors. In The EMBO journal 33 (14), pp. 1582-1598. DOI: 10.15252/embj.201387579.

Thyrock, Anika; Ossendorf, Edith; Stehling, Martin; Kail, Mark; Kurtz, Tanja; Pohlentz, Gottfried et al. (2013): A new Mint1 isoform, but not the conventional Mint1, interacts with the small GTPase Rab6. In PloS one 8 (5), e64149. DOI: 10.1371/journal.pone.0064149.

Trgovcich, Joanne; Cebulla, Colleen; Zimmerman, Pete; Sedmak, Daniel D. (2006): Human cytomegalovirus protein pp71 disrupts major histocompatibility complex class I cell surface expression. In Journal of virology 80 (2), pp. 951-963. DOI: 10.1128/JVI.80.2.951-963.2006.

Troncone, Luca; Luciani, Marco; Coggins, Matthew; Wilker, Elissa H.; Ho, Cheng-Ying; Codispoti, Kari Elise et al. (2016): AB Amyloid Pathology Affects the Hearts of Patients With Alzheimer's Disease. Mind the Heart. In Journal of the American College of Cardiology 68 (22), pp. 2395-2407. DOI: 10.1016/j.jacc.2016.08.073.

Turner, James E.; Campbell, John P.; Edwards, Kate M.; Howarth, Lauren J.; Pawelec, Graham; Aldred, Sarah et al. (2014): Rudimentary signs of immunosenescence in Cytomegalovirus-seropositive healthy young adults. In Age (Dordrecht, Netherlands) 36 (1), pp. 287-297. DOI: 10.1007/s11357-013-9557-4.

Vernooij, M. W .; van der Lugt, A.; Ikram, M. A.; Wielopolski, P. A.; Niessen, W. J.; Hofman, A. et al. (2008): Prevalence and risk factors of cerebral microbleeds. The Rotterdam Scan Study. In Neurology 70 (14), pp. 1208-1214. DOI: 10.1212/01.wnl.0000307750.41970.d9.

Vogt, Nicholas M.; Kerby, Robert L.; Dill-McFarland, Kimberly A.; Harding, Sandra J.; Merluzzi, Andrew P.; Johnson, Sterling C. et al.

(56) References Cited

PUBLICATIONS (2017): Gut microbiome alterations in Alzheimer's disease. In Scientific reports 7 (1), p. 13537. DOI: 10.1038/s41598-017-13601-y.

Waisner, Hope; Kalamvoki, Maria (2019): The ICP0 Protein of Herpes Simplex Virus 1 (HSV-1) Downregulates Major Autophagy Adaptor Proteins Sequestosome 1 and Optineurin during the Early Stages of HSV-1 Infection. In J Virol 93 (21). DOI: 10.1128/JVI.01258-19.

Wang, Baiping; Yang, Li; Wang, Zilai; Zheng, Hui (2007): Amyoild precursor protein mediates presynaptic localization and activity of the high-affinity choline transporter. In Proceedings of the National Academy of Sciences 104 (35), pp. 14140-14145. DOI: 10.1073/pnas.0704070104.

White, H.; Pieper, C.; Schmader, K.; Fillenbaum, G. (1997): A longitudinal analysis of weight change in Alzheimer's disease. In Journal of the American Geriatrics Society 45 (4), pp. 531-532. DOI: 10.1111/j.1532-5415.1997.tb05187.x.

Wong, Bruce X.; Tsatsanis, Andrew; Lim, Linh Q.; Adlard, Paul A.; Bush, Ashley I.; Duce, James A. (2014): β-Amyloid precursor protein does not possess ferroxidase activity but does stabilize the cell surface ferrous iron exporter ferroportin. In PloS one 9 (12), e114174. DOI: 10.1371/journal.pone.0114174.

Yamamoto, Shinya; Charng, Wu-Lin; Bellen, Hugo J. (2010): Endocytosis and intracellular trafficking of Notch and its ligands. In Current topics in developmental biology 92, pp. 165-200. DOI: 10.1016/S0070-2153(10)92005-X.

Yang, Yi; Willis, Thea L.; Button, Robert W.; Strang, Conor J.; Fu, Yuhua; Wen, Xue et al. (2019): Cytoplasmic DAXX drives SQSTM1/p62 phase condensation to activate Nrf2-mediated stress response. In Nature communications 10 (1), p. 3759. DOI: 10.1038/s41467-019-11671-2.

Raghavan B, Cook CH, Trgovcich J. The carboxy terminal region of the human cytomegalovirus immediate early 1 (IE1) protein disrupts type II inteferon signaling. Viruses. Apr. 2, 2014;6(4):1502-24. doi: 10.3390/v6041502. PMID: 24699362; PMCID: PMC4014707.

Ables, Jessica L.; Breunig, Joshua J.; Eisch, Amelia J.; Rakic, Pasko (2011): Not(ch) just development. Notch signaling in the adult brain. In Nature reviews. Neuroscience 12 (5), pp. 269-283. DOI: 10.1038/nrn3024.

Amtul, Zareen; Lewis, Patrick A.; Piper, Sian; Crook, Richard; Baker, Matt; Findlay, Kirk et al. (2002): A presenilin 1 mutation associated with familial frontotemporal dementia inhibits gamma-secretase cleavage of APP and notch. In Neurobiology of Disease 9 (2), pp. 269-273. DOI: 10.1006/nbdi.2001.0473.

Bell, S. P.; Liu, D.; Samuels, L. R.; Shah, A. S.; Gifford, K. A.; Hohman, T. J.; Jefferson, A. L. (2017): Late-Life Body Mass Index, Rapid Weight Loss, Apolipoprotein E ε4 and the Risk of Cognitive Decline and Incident Dementia. In The journal of nutrition, health & aging 21 (10), pp. 1259-1267. DOI: 10.1007/s12603-017-0906-3.

Bhat, Rekha; Crowe, Elizabeth P.; Bitto, Alessandro; Moh, Michelle; Katsetos, Christos D.; Garcia, Fernando U. et al. (2012): Astrocyte senescence as a component of Alzheimer's disease. In PloS one 7 (9), e45069. DOI: 10.1371/journal.pone.0045069.

Bogdanow, Boris; Weisbach, Henry; Einem, Jens von; Straschewski, Sarah; Voigt, Sebastian; Winkler, Michael et al. (2013): Human cytomegalovirus tegument protein pp150 acts as a cyclin A2-CDK-dependent sensor of the host cell cycle and differentiation state. In Proceedings of the National Academy of Sciences of the United States of America 110 (43), pp. 17510-17515. DOI: 10.1073/pnas.1312235110.

Cataldo, Anne M.; Petanceska, Suzana; Terio, Nicole B.; Peterhoff, Corrinne M.; Durham, Robert; Mercken, Marc et al. (2004): Abeta localization in abnormal endosomes. Association with earliest Abeta elevations in AD and Down syndrome. In Neurobiology of aging 25 (10), pp. 1263-1272. DOI: 10.1016/j.neurobiolaging.2004.02.027.

Chakrabarty, Paramita; Li, Andrew; Ceballos-Diaz, Carolina; Eddy, James A.; Funk, Cory C.; Moore, Brenda et al. (2015): IL-10 alters immunoproteostasis in APP mice, increasing plaque burden and worsening cognitive behavior. In Neuron 85 (3), pp. 519-533. DOI: 10.1016/j.neuron.2014.11.020.

Chen, Qian; Zhou, Zhou; Zhang, Lei; Xu, Shangcheng; Chen, Chunhai; Yu, Zhengping (2014): The cellular distribution and Ser262 phosphorylation of tau protein are regulated by BDNF in vitro. In PloS one 9 (3), e91793. DOI: 10.1371/journal.pone.0091793.

Choy, Regina Wai-Yan; Cheng, Zhiliang; Schekman, Randy (2012): Amyloid precursor protein (APP) traffics from the cell surface via endosomes for amyloid β (Aβ) production in the trans-Golgi network. In Proceedings of the National Academy of Sciences of the United States of America 109 (30), E2077-82. DOI: 10.1073/pnas.1208635109.

Ciani, Miriam; Bonvicini, Cristian; Scassellati, Catia; Carrara, Matteo; Maj, Carlo; Fostinelli, Silvia et al. (2019): The Missing Heritability of Sporadic Frontotemporal Dementia. New Insights from Rare Variants in Neurodegenerative Candidate Genes. In International journal of molecular sciences 20 (16). DOI: 10.3390/ijms20163903.

Cronin, Peter; McCarthy, Michael J.; Lim, Andrew S. P.; Salmon, David P.; Galasko, Douglas; Masliah, Eliezer et al. (2017): Circadian alterations during early stages of Alzheimer's disease are associated with aberrant cycles of DNA methylation in BMAL1. In Alzheimer's & dementia : the journal of the Alzheimer's Association 13 (6), pp. 689-700. DOI: 10.1016/j.jalz.2016.10.003.

Zhang, Yun-wu; Chen, Yaomin; Liu, Yun; Zhao, Yingjun; Liao, Francesca-Fang; Xu, Huaxi (2013): APP regulates NGF receptor trafficking and NGF-mediated neuronal differentiation and survival. In PloS one 8 (11), e80571. DOI: 10.1371/journal.pone.0080571.

DelBove, Claire E.; Deng, Xian-Zhen; Zhang, Qi (2018): The Fate of Nascent APP in Hippocampal Neurons. A Live Cell Imaging Study. In ACS chemical neuroscience 9 (9), pp. 2225-2232. DOI: 10.1021/acschemneuro.8b00226.

Di Francesco, Andrea; Arosio, Beatrice; Falconi, Anastasia; Di Micioni Bonaventura, Maria Vittoria; Karimi, Mohsen; Mari, Daniela et al. (2015): Global changes in DNA methylation in Alzheimer's disease peripheral blood mononuclear cells. In Brain, behavior, and immunity 45, pp. 139-144. DOI: 10.1016/j.bbi.2014.11.002.

Dumortier, Jerome; Streblow, Daniel N.; Moses, Ashlee V.; Jacobs, Jon M.; Kreklywich, Craig N.; Camp, David et al. (2008): Human Cytomegalovirus Secretome Contains Factors That Induce Angiogenesis and Wound Healing. In J Virol. 82 (13), pp. 6524-6535. DOI: 10.1128/JVI.00502-08.

Elliott, Evan; Atlas, Roee; Lange, Aya; Ginzburg, Irith (2005): Brain-derived neurotrophic factor induces a rapid dephosphorylation of tau protein through a PI-3 Kinase signalling mechanism. In The European journal of neuroscience 22 (5), pp. 1081-1089. DOI: 10.1111/j.1460-9568.2005.04290.x.

Faux, N. G.; Rembach, A.; Wiley, J.; Ellis, K. A.; Ames, D.; Fowler, C. J. et al. (2014): An anemia of Alzheimer's disease. In Molecular psychiatry 19 (11), pp. 1227-1234. DOI: 10.1038/mp.2013.178.

Fjorback, Anja W.; Seaman, Matthew; Gustafsen, Camilla; Mehmedbasic, Arnela; Gokool, Suzanne; Wu, Chengbiao et al. (2012): Retromer binds the FANSHY sorting motif in SorLA to regulate amyloid precursor protein sorting and processing. In The Journal of neuroscience : the official journal of the Society for Neuroscience 32 (4), pp. 1467-1480. DOI: 10.1523/JNEUROSCI.2272-11.2012.

Fourriere, Lou; Kasri, Amal; Gareil, Nelly; Bardin, Sabine; Bousquet, Hugo; Pereira, David et al. (2019): RAB6 and microtubules restrict protein secretion to focal adhesions. In The Journal of cell biology 218 (7), pp. 2215-2231. DOI: 10.1083/jcb.201805002.

Fu, Yu-Zhi; Su, Shan; Zou, Hong-Mei; Guo, Yi; Wang, Su-Yun; Li, Shu et al. (2019): Human Cytomegalovirus DNA Polymerase Subunit UL44 Antagonizes Antiviral Immune Responses by Suppressing IRF3- and NF-κB-Mediated Transcription. In J Virol 93 (11). DOI: 10.1128/JVI.00181-19.

Grauer, Oliver; Wolff, Daniel; Bertz, Hartmut; Greinix, Hildegard; Kühl, Jörn-Sven; Lawitschka, Anita et al. (2010): Neurological manifestations of chronic graft-versus-host disease after allogeneic haematopoietic stem cell transplantation. Report from the Consen-

(56) References Cited

PUBLICATIONS sus Conference on Clinical Practice in chronic graft-versus-host disease. In Brain : a journal of neurology 133 (10), pp. 2852-2865. DOI: 10.1093/brain/awq245.

Haan, Mary N. (2006): Therapy Insight. Type 2 diabetes mellitus and the risk of late-onset Alzheimer's disease. In Nature clinical practice. Neurology 2 (3), pp. 159-166. DOI: 10.1038/ncpneuro0124.

Heneka, Michael T. (2017): Inflammasome activation and innate immunity in Alzheimer's disease. In Brain pathology (Zurich, Switzerland) 27 (2), pp. 220-222. DOI: 10.1111/bpa.12483.

Hwang, Jiwon; Kalejta, Robert F. (2009): Human cytomegalovirus protein pp71 induces Daxx SUMOylation. In Journal of virology 83 (13), pp. 6591-6598. Doi: 10.1128/JVI.02639-08.

Indran, S. V .; Britt, W. J. (2011): A Role for the Small GTPase Rab6 in Assembly of Human Cytomegalovirus. In Journal of virology 85 (10), pp. 5213-5219. Doi: 10.1128/JVI.02605-10.

Indran, Sabarish V .; Ballestas, Mary E .; Britt, William J. (2010): Bicaudal D1-dependent trafficking of human cytomegalovirus tegument protein pp150 in virus-infected cells. In Journal of virology 84 (7), pp. 3162-3177. Doi: 10.1128/JVI.01776-09.

Kunkle, Brian W .; Grenier-Boley, Benjamin; Sims, Rebecca; Bis, Joshua C .; Damotte, Vincent; Naj, Adam C et al. (2019): Genetic meta-analysis of diagnosed Alzheimer's disease identifies new risk loci and implicates Aß, tau, immunity and lipid processing. In Nature genetics 51 (3), pp. 414-430. DOI: 10.1038/s41588-019-0358-2.

Lee, Hsiang-Ying; Li, Ching-Chia; Juan, Yung-Shun; Chang, Yu-Han; Yeh, Hsin-Chih; Tsai, Chia-Chun et al. (2017): Urinary Incontinence in Alzheimer's Disease. In American journal of Alzheimer's disease and other dementias 32 (1), pp. 51-55. DOI: 10.1177/1533317516680900.

Legoff, Jérôme; Resche-Rigon, Matthieu; Bouquet, Jerome; Robin, Marie; Naccache, Samia N .; Mercier-Delarue, Séverine et al. (2017): The eukaryotic gut virome in hematopoietic stem cell transplantation. New clues in enteric graft- versus-host disease. In Nature medicine 23 (9), pp. 1080-1085. DOI: 10.1038/nm.4380.

Lin, X. P .; Almqvist, N .; Telemo, E. (2005): Human small intestinal epithelial cells constitutively express the key elements for antigen processing and the production of exosomes. In Blood cells, molecules & diseases 35 (2), pp. 122-128. DOI: 10.1016/j.bcmd.2005.05.011.

Liu, Wei Jing; Ye, Lin; Huang, Wei Fang; Guo, Lin Jie; Xu, Zi Gan; Wu, Hong Luan et al. (2016): p62 links the autophagy pathway and the ubiqutin-proteasome system upon ubiquitinated protein degradation. In Cellular & molecular biology letters 21, p. 29. DOI: 10.1186/s11658-016-0031-z.

Liu, Xi-Juan; Yang, Bo; Huang, Sheng-Nan; Wu, Cong-Cong; Li, Xiao-Jun; Cheng, Shuang et al. (2017): Human cytomegalovirus IE1 downregulates Hes1 in neural progenitor cells as a potential E3 ubiquitin ligase. In PLOS pathogens 13 (7), e1006542. DOI: 10.1371/journal.ppat. 1006542.

Rohe, Michael; Hartl, Daniela; Fjorback, Anja Nawarecki; Klose, Joachim; Willnow, Thomas E. (2013): SORLA- mediated trafficking of TrkB enhances the response of neurons to BDNF. In PloS one 8 (8), e72164. DOI: 10.1371/ journal.pone.0072164.

Luganini, Anna; Terlizzi, Maria E.; Gribaudo, Giorgio (2016): Bioactive Molecules Released From Cells Infected with the Human Cytomegalovirus. In Frontiers in microbiology 7, p. 715. DOI: 10.3389/fmich.2016.00715.

Lurain, Nell S.; Hanson, Barbara A.; Martinson, Jeffrey; Leurgans, Sue E.; Landay, Alan L.; Bennett, David A.; Schneider, Julie A. (2013): Virological and immunological characteristics of human cytomegalovirus infection associated with Alzheimer disease. In The Journal of infectious diseases 208 (4), pp. 564-572. DOI: 10.1093/infdis/jit210.

McConlogue, L.; Castellano, F.; deWit, C.; Schenk, D.; Maltese, W. A. (1996): Differential effects of a Rab6 mutant on secretory versus amyloidogenic processing of Alzheimer's beta-amyloid precursor protein. In Journal of Biological Chemistry 271 (3), pp. 1343-1348. DOI: 10.1074/jbc.271.3.1343.

Mehmedbasic, Arnela; Christensen, Sofie K.; Nilsson, Jonas; Rüetschi, Ulla; Gustafsen, Camilla; Poulsen, Annemarie Svane Aavild et al. (2015): SorLA complement-type repeat domains protect the amyloid precursor protein against processing. In The Journal of biological chemistry 290 (6), pp. 3359-3376. DOI: 10.1074/jbc.M114.619940.

Mercurio, Sara; Serra, Linda; Nicolis, Silvia K. (2019): More than just Stem Cells. Functional Roles of the Transcription Factor Sox2 in Differentiated Glia and Neurons. In International journal of molecular sciences 20 (18). DOI: 10.3390/ijms20184540.

Mocarski, E. S.; Pereira, L.; McCormick, A. L. (1988): Human cytomegalovirus ICP22, the product of the HWLF1 reading frame, is an early nuclear protein that is released from cells. In The Journal of general virology 69 (Pt 10), pp. 2613-2621. DOI: 10.1099/0022-1317-69-10-2613.

Moh, Calvin; Kubiak, Jacek Z.; Bajic, Vladan P.; Zhu, Xiongwei; Smith, Mark A.; Lee, Hyoung-Gon (2011): Cell cycle deregulation in the neurons of Alzheimer's disease. In Results and problems in cell differentiation 53, pp. 565-576. DOI: 10.1007/978-3-642-19065-0_23.

Moreno-Jiménez, Elena P.; Flor-García, Miguel; Terreros-Roncal, Julia; Rábano, Alberto; Cafini, Fabio; Pallas-Bazarra, Noemí et al. (2019): Adult hippocampal neurogenesis is abundant in neurologically healthy subjects and drops sharply in patients with Alzheimer's disease. In Nature medicine 25 (4), pp. 554-560. DOI: 10.1038/s41591-019-0375-9.

Morgan, Angharad R.; Touchard, Samuel; Leckey, Claire; O'Hagan, Caroline; Nevado-Holgado, Alejo J.; Barkhof, Frederik et al. (2019): Inflammatory biomarkers in Alzheimer's disease plasma. In Alzheimer's & dementia : the journal of the Alzheimer's Association 15 (6), pp. 776-787. DOI: 10.1016/j.jalz.2019.03.007.

Nakamura, Akinori; Kaneko, Naoki; Villemagne, Victor L.; Kato, Takashi; Doecke, James; Doré, Vincent et al. (2018): High performance plasma amyloid-β biomarkers for Alzheimer's disease. In Nature 554 (7691), pp. 249-254. DOI: 10.1038/nature25456.

Nho, Kwangsik; Kueider-Paisley, Alexandra; Ahmad, Shahzad; MahmoudianDehkordi, Siamak; Arnold, Matthias; Risacher, Shannon L. et al. (2019): Association of Altered Liver Enzymes With Alzheimer Disease Diagnosis, Cognition, Neuroimaging Measures, and Cerebrospinal Fluid Biomarkers. In JAMA network open 2 (7), e197978. DOI: 10.1001/jamanetworkopen.2019.7978.

Patwardhan, Anand; Bardin, Sabine; Miserey-Lenkei, Stéphanie; Larue, Lionel; Goud, Bruno; Raposo, Graça; Delevoye, Cédric (2017): Routing of the RAB6 secretory pathway towards the lysosome related organelle of melanocytes. In Nature communications 8, p. 15835. DOI: 10.1038/ncomms15835.

Peila, Rita; Rodriguez, Beatriz L.; Launer, Lenore J. (2002): Type 2 diabetes, APOE gene, and the risk for dementia and related pathologies. The Honolulu-Asia Aging Study. In Diabetes 51 (4), pp. 1256-1262. DOI: 10.2337/diabetes.51.4.1256.

Pottier, C.; Hannequin, D.; Coutant, S.; Rovelet-Lecrux, A.; Wallon, D.; Rousseau, S. et al. (2012): High frequency of potentially pathogenic SORL1 mutations in autosomal dominant early-onset Alzheimer disease. In Molecular psychiatry 17 (9), pp. 875-879. DOI: 10.1038/mp.2012.15.

Redeker, Anke; Remmerswaal, Ester B. M.; van der Gracht, Esmé T. I.; Welten, Suzanne P. M.; Höllt, Thomas; Koning, Frits et al. (2017): The Contribution of Cytomegalovirus Infection to Immune Senescence Is Set by the Infectious Dose. In Frontiers in immunology 8, p. 1953. DOI: 10.3389/fimmu.2017.01953.

Reitz, Christiane; Cheng, Rong; Rogaeva, Ekaterina; Lee, Joseph H.; Tokuhiro, Shinya; Zou, Fanggeng et al. (2011): Meta-analysis of the association between variants in SORL1 and Alzheimer disease. In Archives of neurology 68 (1), pp. 99-106. DOI: 10.1001/archneurol.2010.346.

Rogaeva, Ekaterina; Meng, Yan; Lee, Joseph H.; Gu, Yongjun; Kawarai, Toshitaka; Zou, Fanggeng et al. (2007): The neuronal sortilin-related receptor SORL1 is genetically associated with Alzheimer disease. In Nature genetics 39 (2), pp. 168-177. DOI: 10.1038/ng1943.

(56) References Cited

PUBLICATIONS

Janas T, et al., Mechanisms of RNA loading into exosomes. FEBS Lett. Jun. 4, 2015;589(13):1391-8. doi: 10.1016/j.febslet.2015.04. 036. Epub Apr. 30, 2015. PMID: 25937124.

Guzman-Flores JE, et al., Proteomic analysis of Escherichia coli detergent-resistant membranes (Drm). PloS One. Oct. 11, 2019;14(10):e0223794. doi: 10.1371/journal.pone.0223794. PMID: 31603938; PMCID: PMC6788730.

Malabirade A, et al., Membrane association of the bacterial riboregulator Hfq and functional perspectives. Sci Rep. Sep. 6, 2017;7(1):10724. doi: 10.1038/s41598-017-11157-5. Erratum in: Sci Rep. Nov. 10, 2017;7(1):15651. PMID: 28878270; PMCID: PMC5587644.

Ito M, et al., Herpes Simplex Virus Type 1 Induces Apoptosis in Peripheral Blood T Lymphocytes, The Journal of Infectious Diseases, vol. 175, Issue 5, May 1997, pp. 1220-1224, https://doi.org/10.1086/593672.

Guoping P, et al., Characteristics of the peripheral T cell immune response of patients at different stages of vascular cognitive impairment. Immunol Lett. Nov. 2015;168(1):120-5. doi: 10.1016/j.imlet. 2015.09.015. Epub Oct. 26, 2015. PMID: 26433058.

Ciccocioppo F., et al., The Characterization of Regulatory T-Cell Profiles in Alzheimer's Disease and Multiple Sclerosis. Sci Rep. Jun. 19, 2019;9(1):8788. doi: 10.1038/s41598-019-45433-3. PMID: 31217537; PMCID: PMC6584558.

Wu Ca, Shanley, JD., Chronic infection of human umbilical vein endothelial cells by human herpesvirus-6. J Gen Virol. May 1998;79 ( Pt 5):1247-56. doi: 10.1099/0022-1317-79-5-1247. PMID: 9603340.

Jones K, et al., Infection of human endothelial cells with Epstein-Barr virus. J Exp Med. Nov. 1, 1995; 182(5):1213-21. doi: 10.1084/jem.182.5.1213. PMID: 7595192; PMCID: PMC2192185.

Sindre H, et al., Human intestinal endothelium shows high susceptibility to cytomegalovirus and altered expression of adhesion molecules after infection. Scand J Immunol. Apr. 2000;51(4):354-60. doi: 10.1046/j.1365-3083.2000.00676.x. PMID: 10736107.

Key NS, et al., Infection of vascular endothelial cells with herpes simplex virus enhances tissue factor activity and reduces thrombomodulin expression. Proc Natl Acad Sci U S A. Sep. 1990;87(18):7095-9. doi: 10.1073/pnas.87.18.7095. PMID: 2169619; PMCID: PMC54690.

Arora M, Goldberg EM. Kaposi sarcoma involving the gastrointestinal tract. Gastroenterol Hepatol (N Y). Jul. 2010; 6(7): 459-62. PMID: 20827371; PMCID: PMC2933764.

Lavery, EA, Coyle WJ. Herpes simplex virus and the alimentary tract. Curr Gastroenterol Rep. Aug. 2008;10(4):417-23. doi: 10.1007/s11894-008-0078-8. PMID: 18627656.

Ryan JL, et al., Epstein-Barr virus infection is common in inflamed gastrointestinal mucosa. Dig Dis Sci. Jul. 2012;57(7):1887-98. doi: 10.1007/s10620-012-2116-5. Epub Mar. 13, 2012. PMID: 22410851; PMCID: PMC3535492.

Halme L, et al., Human Herpesvirus 6 Infection of the Gastroduodenal Mucosa, Clinical Infectious Diseases, vol. 46, Issue 3, Feb. 1, 2008, pp. 434-439, https://doi.org/10.1086/525264.

Iadecola, C. The overlap between neurodegenerative and vascular factors in the pathogenesis of dementia. Acta Neuropathol. Sep. 2010;120(3):287-96. doi: 10.1007/s00401-010-0718-6. Epub Jul. 11, 2010. PMID: 20623294; PMCID: PMC3001188.

Young, Vivian, Detection of HCMV viral IL-10 (vIL-10) in healthy blood donors; Master's Thesis at University of San Francisco 2015, https://repository.usfca.edu/cgi/viewcontent.cgi?article=1182&context=thes.

Huang, Hsing-I et al., Exosomes Facilitate Transmission of Enterovirus A71 From Human Intestinal Epithelial Cells, The Journal of Infectious Diseases, vol. 222, Issue 3, Aug. 1, 2020, pp. 456-469, https://doi.org/10.1093/infdis/jiaa174.

Sochocka, M, et al., The Gut Microbiome Alterations and Inflammation-Driven Pathogenesis of Alzheimer's Disease—a Critical Review. Mol Neurobiol. Mar. 2019;56(3):1841-1851. doi: 10.1007/s12035-018-1188-4. Epub Jun. 23, 2018. PMID: 29936690; PMCID: PMC6394610.

Janus T, et al., Specific RNA binding to ordered phospholipid bilayers. Nucleic Acids Res. Apr. 26, 2006;34(7):2128-36. doi: 10.1093/nar/gkl220. PMID: 16641318; PMCID: PMC1449910.

Koeppen, K, et al., A Novel Mechanism of Host-Pathogen Interaction through sRNA in Bacterial Outer Membrane Vesicles. PLoS Pathog. Jun. 13, 2016; 12(6):e1005672. doi: 10.1371/journal.ppat. 1005672. PMID: 27295279; PMCID: PMC4905634.

Choi, JW, et al., Secretable Small RNAs via Outer Membrane Vesicles in Periodontal Pathogens. J Dent Res. Apr. 2017;96(4):458-466. doi: 10.1177/0022034516685071. Epub Jan. 9, 2017. PMID: 28068479.

Ashraf, U. et al., MicroRNA-19b-3p Modulates Japanese Encephalitis Virus-Mediated Inflammation via Targeting RNF11. J Virol. Apr. 14, 2016;90(9):4780-4795. doi: 10.1128/JVI.02586-15. PMID: 26937036; PMCID: PMC4836334.

Deng, L., et al., Modulation of miR-185-5p expression by EBV-miR-BART6 contributes to developmental differences in ABCG4 gene expression in human megakaryocytes. Int J Biochem Cell Biol. Dec. 2016;81(Pt A):105-111. doi:10.1016/j.biocel.2016.11.001. Epub Nov. 2, 2016. PMID: 27816548.

Kumar A., et al., MicroRNA hsa-miR-324-5p Suppresses H5N1 Virus Replication by Targeting the Viral PB1 and Host CUEDC2. J Virol. Sep. 12, 2018;92(19):e01057-18. doi: 10.1128/JVI.01057-18. PMID: 30045983; PMCID: PMC6146810.

Moyano A.L. et al., Bongarzone ER. microRNA-219 Reduces Viral Load and Pathologic Changes in Theiler's Virus-Induced Demyelinating Disease. Mol Ther. Mar. 7, 2018;26(3):730-743. doi: 10.1016/j.ymthe.2018.01.008. Epub Jan. 17, 2018. PMID: 29433936; PMCID: PMC5910888.

Lee et al., BclAF1 restriction factor is neutralized by proteasomal degradation and microRNA repression during human cytomegalovirus infection, PNAS, 2012, Jun. 12, 9575-9580, 109(24).

Qin et al., Bclaf1 critically regulates the type I interferon response and is degraded by alphaherpesvirus US3, PLoS Pathog, Jan. 25, 2019, e1007559, 15(1).

Maidji et al., Replication of CMV in the gut of HIV individualsand epithelial barrier dysfunction, 2017, PLos Path. 13(2) e1006202.

Reuter et al., The ND10 Component Promyelocytic Leukemia Protein Acts as an E3 Ligase for SUMOylation of the Major Immediate Early Protein IE1 of Human Cytomegalovirus. J Virol. Apr. 28, 2017:e02335-16, 91(10).

Lu et al., Stimulation of the Replication of ICP0-Null Mutant Herpes Simplex Virus 1 and pp71-Deficient Human Cytomegalovirus by Epstein-Barr Virus Tegument Protein BNRF1, Journal of Virology, Nov. 2016., 9964-9673, 90 (21).

Lee et al., BcIAF1 restriction factor is neutralized by proteasomal degradation and microRNA repression during human cytomegalovirus infection, PNAS, Jun. 12, 2012, 9575-9580, 109(24).

Qin et al., Bclaf1 critically regulates the type I interferon response and is degraded by alphaherpesvirus US3, PLoS Pathog, Jan. 25, 2019, e1007559, 15(1).

Sjöström et al., Membrane vesicle-mediated release of bacterial RNA, Sci. Rep. Oct. 5, 2015;15329, pp. 1-10.

Ghosal et al., The extracellular complement of Escherichia coli, Microbiology Open, 2015, 4(2), 252-266.

Resch et al., A two-component regulatory system impacts extracellular membrane-derived vesicle production in group A Streptococcus, mBio, Nov. 2016, 7(6), e00207-16.

Barnett et al., Herpes simplex encephalitis in the temporal cortex and limbic system after trigeminal nerve inoculation, J. of Inf. Dis., 1994, 169(4), 782-786.

Di Carlo et al. Unusual MRI findings in an immunocompetent patient with EBV encephalitis: A case report, BMC Med. Imaging 2011, 11(6) 1-4.

Tselis, A.C., Epstein-Barr Virus Infection of the Nervous System, Handbook of Clinical Neurology, 2014, Chapter 13, vol. 123 (3rd series) Neurovirology, A.C. Tselis and J. Booss, Editors, 285-305.

Noguchi et al., MR imaging of human herpesvirus 6 encephalopathy after hematopoietic stem cell transplantation in adults, AJNR 2006, 27(10)2191-2195.

MacLean et al. Severe amnesia associated with human herpesvirus 6 encephalitis after bone marrow transplantation, Transplantation, 2002, 73(7), 1086-1089.

(56) References Cited

PUBLICATIONS

Ribatta, et al., Cytomegalovirus infection in the brain of liver transplant recipients, Liver Transplantation 2003, 9(3) 313-315.

William Khoury-Hanold et al., Viral spread to enteric neurons links genital HSV-1 infection to toxic megacolon and lethality, Cell Host Microbe, Jun. 8, 2017, 19(6): 788-799.

Brun et al. Herpes Simplex Virus Type 1 Infects Enteric Neurons and Triggers Gut Dysfunction via Macrophage Recruitment, Front. Cell. Infect. Microbiol., Mar. 15, 2018, 8, (74).

Stocchi, F. and Torti, M.,Constipation in Parkinson's disease, Int. Rev. Neurobiol. 2017;134: 811-826.

Chen,T. and Hudnall, S.D., Anatomical mapping of human herpesvirus reservoirs of infection, Modern pathology 2006, 19: 726-737.

Friedrich, et al., Mechanisms of lymphatic system-specific viral replication and its potential role in autoimmune disease, Clinical & Experimental Immunology, 2018,195: 64-73. 726-737.

Maidji et al., Replication of CMV in the gut of HIV individualsand epithelial barrer dysfunction, 2017, PLos Path. 13(2) e1006202.

Dennis et al., Cytomegalovirus promotes intestinal macrophage-mediated mucosal inflammationthrough induction of Smad 7, Mucosal Immunity 2018, 11(6) 1694-1704.

Stern, J. et al., Virome and bacteriome: Two sides of the same coin, Curr.Opin.Virol., Aug. 2019; 37: 37-43.

Perumbakkam et al., Marek's disease virus influence the core gut microbiome of the chicken during the early and late phases of viral replication, FEMS Microbiol Ecol., 2014, 90, 300-312.

Besnard et al.,Intestinal pseudo-obstruction and acute pandyautonomia associated with Epstein-Barr virus infection, Journal of Gastroenterology 2000, 95 (1) 280-284.

Ramakrishna et al, Bacteroides fragilis polysaccharide A induces IL-10 secreting B and T cells that prevent viral encephalitis, Nature 2019, 10, 2153.

Tang, W.H.W. and Hazen S.L., The contributory role of gut microbiota in cardiovascular disease,J. of Clinical Invest., Oct. 2014,124;10, pp. 4204-4211.

Yin et al., Dysbiosis of gut microbiota with reduced tramethylamine-N-oxide level in patients with large-artery artherosclerotic stroke or transient ischemic attack, J. Am. Heart Assoc, 2015, 4, e002699.

Vogt et al., The gut microbiota derived metabolite Trimethylamine N-oxide is elevated in Alzheimer's disease, 2018, 10 (124), 1-8.

Miyakawa, T., Electron Microsopy of Amyloid fribils and microvessels, Annals of the New York Academy of Sciences, 1997, 826, 25-34.

Willette et al., Association of insulin resistance with cerebral glucose uptake in late middle-aged adults at risk for Alzheimer's disease, JAMA Neurol. Sep. 1, 2015; 72(9) 1013-1020.

Chen et al., Trimethylamine N-Oxide binds and activates PERK to promote metabolic dysfunction, Cell Metabolism Dec. 3, 2019, 30, 1141-1151.

Chen, et al., A general approach to high-yield biosynthesis of chimeric RNAs bearing various types of functional small RNAs for broad applications, Nucleic Acids Research, Apr. 20, 2015, pp. 3857-3869, vol. 43, Issue 7.

Nelissen et al., Fast production of homogeneous recombinant RNA—towards large-scale production of RNA, Nucleic Acids Research, Jul. 1, 2012, p. e102, vol. 40, Issue 13.

Cui et al., Bacteria-derived outer membrane vesicles engineered with over-expressed pre-miRNA as delivery nanocarriers for cancer therapy. Nanomedicine. Sep. 2022;45:102585.

Choi et al., Secretable Small RNAs via Outer Membrane Vesicles in Periodontal Pathogens. J Dent Res. Apr. 2017;96(4):458-466.

Parry, et al. Cytomegalovirus viral load within blood increases markedly in healthy people over the age of 70 years. Immun Ageing (2016) 13, 1.

Thomasini et al., Aged-associated cytomegalovirus and Epstein-Barr virus reactivation and cytomegalovirus relationship with the frailty syndrome in older women. PLoS ONE, (2017), 12(7): e0180841.

Alonso et al., Infection of Fungi and Bacteria in Brain Tissue From Elderly Persons and Patients With Alzheimer's Disease, Frontiers in Aging Neuroscience, 2018, vol. 10.

Readhead et al., Alzheimer's disease-associated CD83(+) microglia are linked with increased immunoglobulin G4 and human cytomegalovirus in the gut, vagal nerve, and brain, Alzheimer's and Dementia, Jan. 2025, vol. 21, Issue1, e14401.

* cited by examiner

TREATING HERPESVIRUS-MEDIATED INTESTINAL DYSFUNCTION FOR PREVENTION OF AGE-RELATED NEURODEGENERATION

REFERENCE TO THE SEQUENCE LISTING

The instant application contains a sequence listing which has been submitted electronically in ST.25 format and which is hereby incorporated by reference in its entirety. Said sequence listing was created on Jun. 2, 2024, is named 10001B-US-NP-Sequence-Listing and is 72,682 bytes bytes in size.

BACKGROUND

Infection with one or more human herpesviruses (HHVs) is ubiquitous in most populations by the eighth decade of life. HHVs primarily enter the body through trigeminal ganglia or olfactory neurons. Virions shed from these neurons can enter circulating monocytes and dendritic precursors. Circulating monocytes and dendritic precursors differentiate when they encounter inflammatory cytokines. Phagocyte and dendritic cell differentiation reactivates HHV from latency. Apart from replicating reservoirs, HHVs mostly remain latent through the first seven decades. The frequency of HHV reactivation depends on the HHV strain and viral load, and host variables such as stress, age, and genetics. For instance, human cytomegalovirus (HCMV) is an HHV that remains latent but reactivates in individuals experiencing stress, depressed immunity or in healthy individuals over the age of 70. Genetic variants, such as polymorphisms in type 3 interferon, (IFNL3/4) affect susceptibility to HCMV activation.

There are eight known HHVs and each can infect cells residing in the intestinal wall or tract. HCMV (HHV5) replicates in epithelial, fibroblast, endothelial, and dendritic cells. The Epstein-Barr virus (EBV) infects B lymphocytes. The roseolovirus (HHV6/7) causes roseola infantum, and replicates in peripheral blood mononuclear cells (PBMC), NK cells, and T lymphocytes. Herpes simplex virus (HSV) and varicella zoster virus (VZV) replicate in fibroblast, epithelial cells, and sensory neurons.

HHV infections could contribute to developing Alzheimer's disease, Parkinson's disease, Lewy body dementia, vascular dementia, frontotemporal dementia, and amyotrophic lateral sclerosis. A causal relationship between HHV infection and age-related neurodegeneration remains unproven. Researchers have found no HHV association with age-neurodegenerations, and those that have reported an association have not proven causation. Interestingly, congenital HCMV infections with severe brain degeneration show a conspicuous absence of viral DNA, which suggests that a non-cell autonomous bystander effect mediates significant pathology. This could explain why some studies failed to find a difference in HHV between brains from control and neurodegeneration patients. The scenario is reminiscent of the HIV-associated neurocognitive disorder mediated by the HIV protein TAT. Association by seropositivity is also problematic. HCMV seronegative subjects can test PCR positive for HCMV DNA in blood, and seropositive subjects can consistently test PCR negative for HCMV DNA. Hcmv can also reactivate intermittently in short intervals, so blood HCMV DNA might be negative one week and positive the next. Thus, researchers may have erroneously concluded no association exists between some HHVs and age-related neurodegeneration.

Furthermore, HHVs, like HCMV, infect immune cells, and their infection status is associated with oxidative stress, shortened telomeres of lymphocytes, reduced B cell lineages, and T-cell senescence. The subsequent effects of HHV infection on immunity may increase host susceptibility to other opportunistic infections, which are associated with age-related neurodegeneration. Impaired immunity may affect the diversity of symbiotic gut microbiota. Indeed, Alzheimer's disease patients have reduced microbial diversity. A human host utilizes factors manufactured by gut bacteria. For instance, some bacterial strains produce gamma-aminobutyric acid (GABA), which is thought to be transported to the brain. GABA is an inhibitory neurotransmitter reported to be deficient in brains of Alzheimer's disease patients. Accordingly, the pathogenesis of some neurodegenerations may not originate in the brain.

SUMMARY OF THE INVENTION

Alteration in gut microbiota and gastrointestinal tract inflammation can have deleterious health effects. Human herpesvirus infection of cells related to gastrointestinal system can cause intestinal inflammation, microbiota dysbiosis, barrier dysfunction, microbial-translocation, and neurodegeneration. The invention describes treatments for preventing or treating intestinal dysfunction caused by human herpesviruses by the oral delivery of exosomes, or the ingestion of recombinant bacteria engineered to release therapeutic factors in exosomes. Treatments such as described will at last provide therapy to prevent, delay, or cure age-related neurodegenerations derived from an unsuspected cause, intestinal herpesvirus infection.

DETAILED DESCRIPTION

In addition to the HHV association noted in the Background, age-related neurodegeneration is associated with gut microbiota dysbiosis. HHV infection of B lymphocytes, T-cells, dendritic cells, and PBMCs can compromise intestinal immunity and increase pathogen-mediated inflammation. Increased inflammation is associated with gut microbiota dysbiosis, where the prevalence of healthy symbiotic bacteria is decreased, and pathogenic bacteria increased. Accordingly, HHV infection is associated with colitis and exacerbated ulcerative colitis in healthy immunocompetent patients. Age-related neurodegeneration has also been associated with genetic variants affecting innate immunity and microbial agents. HHV infection of intestinal epithelial cells, vascular endothelial cells, and fibroblasts can compromise the intestinal barrier and allow microbial translocation.

HHV infection can cause oxidative stress that may over time accelerate stem cell senescence. Additionally, HHV is associated with impaired the Wnt/β-catenin signaling and loss of β-catenin-mediated gene transcription; β-catenin is required for epithelial cell specification, maintenance, and replication. Replicative senescence of transiently replicating epithelium and stem cells can decrease barrier function. Decreased barrier function, often called "leaky gut", can permit microbial translocation. The elderly with reduced immunity and or compromised blood-brain-barrier are at increased risk for microbes entering the brain. Microbial infection in the brain can initiate an inflammatory response that causes age-related neurodegeneration. Further, with advanced age, the inflammatory response is more sustained. Inflammatory bowel diseases, such as Crohn's disease and ulcerative colitis, are associated with a leaky gut, and accordingly, are associated with an increased rate of Parkinson's disease. Genetic variants that increase the risk of Crohn's disease are also associated with Parkinson's disease. Mice injected with gut bacteria from Parkinson's disease patients develop neuronal α-synuclein clumping and behavioral symptoms supporting a microbial translocation etiology of Parkinson's disease. Further support of a gut-related etiology for Parkinson's disease comes from the presence of α-synuclein aggregates within the enteric nerve terminals of every examined Parkinson's disease patient. Compared to healthy age-matched controls, Parkinson's disease patients also have reduced occludin protein, a component of tight junctions which could disrupt the intestinal epithelial barrier.

Parkinson's disease patients have significantly more serum HSV IgG antibodies compared to controls, P<0.001. HSV1 DNA was found in the celiac ganglia of a transplant patient and detected in the ganglia innervating the gastrointestinal tract in eight out of ten subjects. In mouse models of enteric HSV1 infection, macrophages-recruited to HSV1 infected neurons release reactive nitrogen species causing neuron injury. Injury to enteric plexus neurons by HHV-infection can explain the most frequent symptom of Parkinson's disease patients, constipation.

A variety of translocated microbes could explain the heterogenous nature of age-related neurodegeneration. Microbe phagocytosis by antigen-presenting cells selects an immunogen to initiate an immune response. If a host protein has a similar sequence to a microbial epitope, it will cross-react and cause autoimmune disease by mimicry. For instance, a UniProt blast of tau protein against bacterial proteasomes identified bacteria with high sequence similarity to proteins from bacterial strains of *Actinomyces, Streptococcus,* and *Streptomyces*. The α-synuclein protein, which forms aggregates in Parkinson's disease patients, has sequence-similarity to proteins found in fecal bacteria. A-UniProt blast of α-synuclein against microbial proteomes identified sequence similarity with the uncharacterized protein from the Verrucomicrobia bacterium, with 43.7% positives (2.3e-04 E-value), and with similarity to the chromosome segregation ATPase from *Bifidobacterium*, with 47% positives (1.4e-03 E-value).

Anti-α-synuclein IgG2 is significantly increased in the plasma from Parkinson's disease patients. IgG2 increases in response to bacterial infections and reacts to bacterial polysaccharides. Intracellular antibodies can cause target aggregation, which are both degraded by the proteasome. Proteasome degradation slows with aging, which could explain age-related onset of age-related neurodegeneration. It is not known whether IgG physically associates with age-related neurodegeneration related-protein aggregates. However, levels of antinuclear antibodies increase with age and are associated with signs of senescence, e.g., telomere shortening. Antinuclear antibodies, indicative for autoimmune disease, are frequently associated with herpes simplex encephalitis.

A chronic subclinical HCMV infection in the colon could impair barrier function and allow microbial translocation. Interestingly, Parkinson's disease is associated with significantly less CD8+ T cell senescence compared to age-matched control, which could result if CD8+ T cells do not engage in restricting viral pathogens. Thus, while Parkinson's disease patients can mount an effective cytotoxic CD8+ T immune response against invading microbes, activation requires professional antigen-presenting cells, such as dendritic cells, which may be functionally compromised by HCMV infection.

It is highly likely that enteric sensory neurons harbor HSV and VZV, like the olfactory and trigeminal neurons, and that their reactivation contributes to intestinal inflammation and microbiota dysbiosis. Preventing intestinal HHV activity in intestinal cells can prevent inflammation, microbiota dysbiosis, barrier dysfunction, autoimmune disease, and subsequent age-related neurodegeneration. HSV and VZV infection are treated with nucleoside analogs acyclovir and penciclovir.

There is a long-sought need for an effective Parkinson's disease treatment. Treatment of Parkinson's disease with anti-alpha-HHV nucleoside analogs is not obvious. Unfortunately, long term use of nucleoside analogs can result in HSV and VZV thymidine kinase mutations that render the virus nucleoside resistant. Moreover, HCMV antiviral treatments have serious side-effects, develop resistance, and are not long-term options. A novel method for preventing intestinal HHV-activity through oral delivery exosomes containing stock and customized antiviral factors. Exosomes can be isolated by ultracentrifugation or serial filtration from modified human colonic fibroblast (ATCC-49). Exosomes from colonic fibroblast may contain therapeutic factors for intestinal epithelial cells. For instance, exosomes from a colon fibroblast cell line carry amphiregulin, which binds epidermal growth factor receptor, and rescues intestinal epithelial cells from cell death in organoid culture. HCMV-infected cultured human fibroblasts have markedly altered miRNA expression. Thus, in situ HCMV-infected intestinal niche fibroblasts are likely to have altered exosome content, which may be deleterious to epithelial maintenance. Exosome content from cultured fibroblasts can be customized by inserting donor DNA that encodes pre-miRNAs, mRNA, or long non-coding RNA (lncRNA) into the fibroblast genome using the Sleeping Beauty (SB) transposon system. Construct expression may be driven by fibroblast housekeeping promoters.

Exogenous exosomes might need to penetrate through the mucosal bacteria to enter epithelial cells, vascular endothelial cells, and their respective stem cells. If exosomes do not reach these cells, HHV-activity may be unaffected in these cells. Exosome transfer occurs between the intestinal epithelial cells and bacteria. A novel method to prevent and treat HHV-mediated inflammation, microbiota dysbiosis, barrier dysfunction, autoimmune disease, and subsequent age-related neurodegeneration is to ingest recombinant bacteria that will survive among the gut flora and release exosomes containing antiviral factors. The type of bacteria selected is critical to therapeutic efficacy. The bacteria *Clostridium, Lactobacillus, Enterococcus,* and *Akkermansia* are associated with the mucosal surface, and therefore have the proximity to deliver high concentrations of exosomes with antiviral factors to intestinal cells. The selected bacterial strains may have high genetic tractability. Bacteria are bioengineered to express constructs encoding miRNA, mRNA, and other oligonucleotides using modern techniques for DNA transformation, stable integration by site-specific recombination, and selection. Expression constructs may include coding to direct factors to sort into exosomes for secretion.

In some embodiments, expression constructs are designed to express select Ex-miRNA/shRNA, mRNA, lncRNA and protein as exosome cargo that reduce HHV activity, oxidative stress, inflammation, and increase replicative capacity of intestinal epithelial and vascular endothelial cells. The following are examples of factors delivered in exosomes. In patients with increased HCMV activity, exosomes could include HCMV-miRNAs that suppress active replication.

Human antiviral miRNAs proven to reduce HHV replication include miR-324-5p (SEQ ID NO: 1), miR-185 (SEQ ID NO: 2), miR-29b (SEQ ID NO: 3), miR-1287 (SEQ ID NO: 4), miR-199a-3p (SEQ ID NO: 5), miR-214 (SEQ ID NO: 6), miR-21 (SEQ ID NO: 7), miR-200b-3p (SEQ ID NO: 8), miR-200c-3p (SEQ ID NO: 9), miR-221 (SEQ ID NO: 10) and miR-24-1 (SEQ ID NO: 11). Proteins involved in antiviral defense, such as Sp100 encoded by SEQ ID NO: 12, Daxx encoded by SEQ ID NO: 13, PML encoded by SEQ ID NO: 14, BclAF1 encoded by SEQ ID NO: 15, Tetherin/Bts-2 encoded by SEQ ID NO: 16, Trim 5 alpha encoded by SEQ ID NO: 17, and Apobec-3G encoded by SEQ ID NO: 18, could be delivered as mRNA or protein. For instance, Daxx directs HDAC to the major immediate early gene promoter to silence viral transcription, and BclAF1 is critical for interferon 1 response; both proteins are degraded by HHVs.

An embodiment includes delivering ApoE2/3-ch in exosome. Aside from the autosomal dominant mutations causing early-onset AD, apolipoprotein E (ApoE) allelic variants explain the highest variance in AD risk. The ApoE4 allele confers the greatest AD risk, with ApoE3 neutral, and ApoE2, a protective variant. An explanation for higher AD risk with ApoE4 risk could be related to higher intracellular cholesterol content, especially in lipid rafts, which would increase virion binding affinity. Higher intercellular cholesterol would also provide ample cholesterol for virion assembly. Another explanation is that ApoE2/E3 has less affinity for LDL or LDLR than ApoE4 and may be more available to bind viral glycoproteins or cholesterol both inside and outside the cell. Accordingly, the LDLR and LDL binding domains of ApoE3 can restrict HIV infectivity. The LDLR domain can even protect against early-onset AD from the autosomal dominant mutation, PSEN1, in patients homozygous for the ApoE3-Christchurch mutation (R136S). Moreover, ApoE2/3 is more concentrated in serum than ApoE4. Therefore, delivering ApoE2, for example the sequence encoded by SEQ ID NO: 19 or ApoE3-Christchurch protein for example the sequence encoded by SEQ ID NO: 20, or LDLR domain to intestinal cells via exosomes may protect against HHV infectivity.

An embodiment includes short hairpin RNAs (shRNA) artificially designed to silence HHV gene expression. For instance, a shRNA targeting the HCMV UL83 gene (pp65) at the sequence GCAAGATCTCGCACATCATGC (SEQ ID NO: 21) will reduce pp65 protein expression and release its inhibition on innate and adaptive immunity. Targeting the smallest capsid protein at the sequence GCG-CATGTCCAGTCTGTTTAA (SEQ ID NO: 22) can reduce HCMV yield by 10,000-fold. Additional shRNAs designed to restrict HHV gene expression can be included in the fibroblast and bacteria expression constructs.

Another embodiment includes treating the oxidative stress caused by the HHV. For instance, HCMV increases NAD (P) H oxidase (NOX) activity in endothelial cells, and NOX4 expression is increased in vascular endothelial cells from Alzheimer's disease patients. NOX4 expression is inhibited by miR-137 (SEQ ID NO: 23) and miR-99a (SEQ ID NO: 24). Messenger RNAs encoding proteins that reduce oxidative stress include superoxide dismutase encoded by SEQ ID NO: 25, glutathione reductase encoded by SEQ ID NO: 26, and the protein Hic-5 encoded in SEQ ID NO: 27, which inhibits NOX4 activity by promoting the ubiquitin-proteasome degradation of NOX4.

Another embodiment includes reducing intestinal inflammation by delivering exosome with anti-inflammatory factors. For instance, miR-219a-5p (SEQ ID NO: 28) delivered to T cells downregulates Th1/Th17 cell differentiation. Delivery of miR-146a (SEQ ID NO: 29), miR-19b (SEQ ID NO: 30), miR-590-5p (SEQ ID NO: 31) and miR-495 (SEQ ID NO: 32) may reduce inflammatory cell injury. Delivery of the lncRNA, Mirt2 (SEQ ID NO: 33), to dendritic cells upregulates IL-22 expression and helps resolve chronic inflammation. Macrophages that sense HHV release nitric oxide and inadvertently injure neurons. The microRNA-146a (SEQ ID NO: 29) reduces nitric oxide synthase expression and will reduce nitric oxide release from macrophages.

Another embodiment includes extending the replicative capacity of epithelial and vascular endothelial cells. For instance, HCMV may control replicative senescence of epithelial and endothelial cells. For instance, HCMV infection increases DKK1 expression. DKK1 interacts with Wnt co-receptors LRP5/6, leading to the degradation of β-catenin. Degradation of β-catenin prevents Wnt pathway signaling required for epithelial cell homeostasis and renewal. EBV miRNA, miR-BART10-3p, reduces DKK1 protein expression by 60%. To prevent oncogenic potential, an inducible promoter can be used to drive miR-BART10-3p (SEQ ID NO: 34) expression in recombinant bacteria.

To ensure that miRNAs, mRNA, lncRNA, and protein are sorted to the exosome, the donor DNA may include a 3' export motif, GGAG or GGCU, for hnRNPA2B1 and SYN-CRIP processing respectively. Messenger RNA encoding protein may be directed to the exosome by including a fused ubiquitylated-coding sequence (CTGCC) for ECSRT-dependent processing or a CD63 association sequence for ECSRT-independent processing.

Exosomes from cultured fibroblasts and recombinant bacteria may be isolated by ultracentrifugation or serial filtration to characterize content. Exosome cargo will be tested for the ability to reduce HHV-activity, oxidative stress, inflammation, and induce replication in columnar intestinal epithelial cell cultures. With optimal exosome cargo defined, cultivation of recombinant fibroblast or recombinant bacterial will be scaled for mass production.

HHVs reactivate during immunosuppression, such as with transplant or chemotherapy, to cause life-threatening disease. The described novel treatments are useful for restricting HHV-mediated intestinal disease and may be administered prophylactically in immunosuppressed patients.

The invention claimed is:

1. A method of preventing or treating a human herpesvirus-infection in the gastrointestinal tract of a subject by oral administration of exosomes containing antiviral factors derived from colonic fibroblasts selected from the group consisting of miRNA, shRNA, mRNA, lncRNA, and a combination thereof.

2. The method according to claim 1, wherein the human herpesvirus-infection is intestinal.

3. The method according to claim 1, wherein the human herpesvirus type treated is selected from the group consisting of human cytomegalovirus, herpes simplex virus 1, herpes simplex virus 2, Epstein-Barr virus, varicella zoster virus, roseolovirus (HHV 6, HHV7), Kaposi sarcoma virus (HHV8), and a combination thereof.

4. The method according to claim 1, wherein the exosome includes mRNAs encoding antiviral proteins selected from the group consisting of Sp100 (SEQ ID NO:12), Daxx (SEQ ID NO:13), PML (SEQ ID NO:14), BclAF1 (SEQ ID NO:15), or a combination thereof.

5. The method of claim 1, wherein the exosome antiviral factors silence human herpesvirus gene expression.

6. The method according to claim 5, wherein the expression of the human cytomegalovirus protein pp65 is silenced using a shRNA targeting sequence of SEQ ID NO: 21 and/or the expression of the human cytomegalovirus smallest capsid protein is silence using a shRNA targeting sequence of SEQ ID NO: 22.

7. A method of preventing or treating human herpesvirus infection in the gastrointestinal tract of a subject, the method comprising the oral administration of recombinant gram-negative bacteria engineered to contain a genome-integrated expression construct for expression of antiviral protein, miRNA, or both, that are exported in vesicles.

8. The method according to claim 7, wherein the recombinant bacteria are derived from the genus *Akkermansia*.

9. The method according to claim 7, wherein the human herpesvirus type is selected from the group consisting of human cytomegalovirus, herpes simplex virus 1, herpes simplex virus 2, Epstein-Barr virus, varicella zoster virus, roseolovirus (HHV 6, HHV7), HHV8, and a combination thereof.

10. The method according to claim 7, wherein the expression construct is under the control of an inducible promoter.

11. The method according to claim 7, wherein the genome-integrated expression construct encodes mRNA translated into an antiviral protein selected from the group consisting of Sp100 (SEQ ID NO:12), Daxx (SEQ ID NO:13), PML (SEQ ID NO:14), and BclAF1 (SEQ ID NO: 15).

12. The method according to claim 7, wherein the antiviral factors the recombinant bacteria expression construct encodes are short hairpin RNAs (shRNAs) designed to reduce human herpesvirus gene expression.

13. The method according to claim 12, wherein the human herpesvirus gene silenced is human cytomegalovirus pp65 using the shRNA target sequence in SEQ ID NO: 21 and/or the smallest capsid protein using shRNA target sequence in SEQ ID NO: 22.

14. The method of claim 1, wherein the antiviral factors are selected from a group consisting of, hsa-miR-185 (SEQ ID NO:2), hsa-miR-199a-3p (SEQ ID NO:5), hsa-miR-200b-3p (SEQ ID NO:8), hsa-miR-200c-3p (SEQ ID NO:9), hsa-miR-24-1 (SEQ ID NO: 11), hsa-miR-219a-5p (SEQ ID NO: 28), and a combination thereof.

15. The method of claim 7, wherein the antiviral factors are selected from a group consisting of hsa-miR-185 (SEQ ID NO:2), hsa-miR-199a-3p (SEQ ID NO:5), hsa-miR-200b-3p (SEQ ID NO:8), hsa-miR-200c-3p (SEQ ID NO:9), hsa-miR-24-1 (SEQ ID NO:11), hsa-miR-219a-5p (SEQ ID NO: 28), and a combination thereof.

16. The method of claim 1, wherein the mRNA is selected from the group consisting of ApoE2 allele (SEQ ID NO: 19) the ApoE3-Christchurch allele (SEQ ID NO: 20), and a combination thereof.

17. The method of claim 7, wherein the bacteria are engineered to express proteins encoded by an mRNA selected from the group consisting of ApoE2 allele (SEQ ID NO: 19) the ApoE3-Christchurch allele (SEQ ID NO: 20), and a combination thereof.

* * * * *

SEQUENCE LISTING

```
<160> NUMBER OF SEQ ID NOS: 37

<210> SEQ ID NO 1
<211> LENGTH: 22
<212> TYPE: DNA
<213> ORGANISM: Homo sapiens
<300> PUBLICATION INFORMATION:
<301> AUTHORS: Kim J. et al.
```

```
<302> TITLE: Identification of many microRNAs...
<303> JOURNAL: Proc Natl Acad Sci U S A
<304> VOLUME: 101
<305> ISSUE: 1
<306> PAGES: 360-365
<307> DATE: 2004-01-06
<308> DATABASE ACCESSION NUMBER: www.mirbase.org/MIMAT0000761
<309> DATABASE ENTRY DATE: 2018-10-01
<313> RELEVANT RESIDUES IN SEQ ID NO: (1)..(22)

<400> SEQUENCE: 1
cgcauccccu agggcauugg ug                                              22

<210> SEQ ID NO 2
<211> LENGTH: 63
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000482
<309> DATABASE ENTRY DATE: 2018-10-18
<313> RELEVANT RESIDUES IN SEQ ID NO: (15)..(37)

<400> SEQUENCE: 2
gggggcgagg gaggagagaa aggcagccga ggccccccc aggggcggcc ccggcccccc      60
cca                                                                   63

<210> SEQ ID NO 3
<211> LENGTH: 80
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000105
<309> DATABASE ENTRY DATE: 2018-10-01
<313> RELEVANT RESIDUES IN SEQ ID NO: (10)..(33)

<400> SEQUENCE: 3
uucaggaagc ugguuucaua uggugguuua gauuuaaaua gugauugucu agcaccauuu      60
gaaaucagug uucuuggggg                                                 80

<210> SEQ ID NO 4
<211> LENGTH: 90
<212> TYPE: DNA
<213> ORGANISM: Homo sapiens
<300> PUBLICATION INFORMATION:
<301> AUTHORS: Morin R.D., et al.
<302> TITLE: Application of massively parallel sequencing to microRNA...
<303> JOURNAL: Genome Res.
<304> VOLUME: 18
<305> ISSUE: 4
<306> PAGES: 610-621
<307> DATE: 2008-04-01
<308> DATABASE ACCESSION NUMBER: www.mirbase.org/MI0006349
<309> DATABASE ENTRY DATE: 2018-10-01
<313> RELEVANT RESIDUES IN SEQ ID NO: (16)..(38)

<400> SEQUENCE: 4
```

```
guugugcugu ccaggugcug gaucaguggu ucgagucuga gccuuuaaaa gccacucuag    60
ccacagaugc agugauugga gccaugacaa                                    90

<210> SEQ ID NO 5
<211> LENGTH: 22
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MIMAT0000232
<309> DATABASE ENTRY DATE: 2018-10-01
<313> RELEVANT RESIDUES IN SEQ ID NO: (1)..(22)

<400> SEQUENCE: 5
acaguagucu gcacauuggu ua                                            22

<210> SEQ ID NO 6
<211> LENGTH: 109
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000290
<309> DATABASE ENTRY DATE: 2018-10-01
<313> RELEVANT RESIDUES IN SEQ ID NO: (71)..(92)

<400> SEQUENCE: 6
gccuggcugg acagaguugu caugugucug ccugucuaca cuugcugugc agaacauccg    60
cucaccugua cagcaggcac agacaggcag ucaugacaa acccagccu                109

<210> SEQ ID NO 7
<211> LENGTH: 72
<212> TYPE: DNA
<213> ORGANISM: Homo sapiens
<300> PUBLICATION INFORMATION:
<301> AUTHORS: Landgraf P., et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000077
<309> DATABASE ENTRY DATE: 2018-10-01
<313> RELEVANT RESIDUES IN SEQ ID NO: (8)..(29)

<400> SEQUENCE: 7
ugucggguag cuuaucagac ugauguugac uguugaaucu cauggcaaca ccagucgaug    60
ggcugucuga ca                                                       72

<210> SEQ ID NO 8
<211> LENGTH: 22
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
```

```
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MIMAT0000318
<309> DATABASE ENTRY DATE: 2018-10-01
<313> RELEVANT RESIDUES IN SEQ ID NO: (1)..(22)

<400> SEQUENCE: 8
uaauacugcc ugguaaugau ga                                      22

<210> SEQ ID NO 9
<211> LENGTH: 23
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MIMAT0000617
<309> DATABASE ENTRY DATE: 2018-10-01
<313> RELEVANT RESIDUES IN SEQ ID NO: (1)..(23)

<400> SEQUENCE: 9
uaauacugcc ggguaaugau gga                                     23

<210> SEQ ID NO 10
<211> LENGTH: 109
<212> TYPE: DNA
<213> ORGANISM: Homo sapiens
<300> PUBLICATION INFORMATION:
<301> AUTHORS: Landgraf P., et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000298
<309> DATABASE ENTRY DATE: 2018-10-01
<313> RELEVANT RESIDUES IN SEQ ID NO: (65)..(87)

<400> SEQUENCE: 10
gaacauccag gucuggggca ugaaccuggc auacaaugua gauuucugug uucguuaggc      60
aacagcuaca uugucugcug gguuucaggc uaccuggaaa cauguucuc                 109

<210> SEQ ID NO 11
<211> LENGTH: 68
<212> TYPE: DNA
<213> ORGANISM: Homo sapiens
<300> PUBLICATION INFORMATION:
<301> AUTHORS: Landgraf P., et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000080
<309> DATABASE ENTRY DATE: 2018-10-01
<313> RELEVANT RESIDUES IN SEQ ID NO: (44)..(65)

<400> SEQUENCE: 11
cuccggugcc uacugagcug auaucaguuc ucauuuuaca cacuggcuca guucagcagg      60
aacaggag                                                              68
```

<210> SEQ ID NO 12
<211> LENGTH: 2050
<212> TYPE: DNA
<213> ORGANISM: Homo sapiens
<300> PUBLICATION INFORMATION:
<301> AUTHORS: Xu P and Roizman B.
<302> TITLE: The SP100 component of ND10 enhances accumulation of PML...
<303> JOURNAL: Proc. Natl. Acad. Sci. U.S.A
<304> VOLUME: 114
<305> ISSUE: 19
<306> PAGES: E3823-E3829
<307> DATE: 2017-04-24
<308> DATABASE ACCESSION NUMBER: genBank/NM_001206704
<309> DATABASE ENTRY DATE: 2008-01-01
<313> RELEVANT RESIDUES IN SEQ ID NO: (1)..(2050)

<400> SEQUENCE: 12

```
agacgctgtg gtctcacctg tcctggcaag gggcctctgc cggctgttcc catgactggc      60
tcagggtctg agttcttatt ccatcaacct tgatcaaaag aaggaaaggg aagaaaaagg     120
cccagggagg ctgaatgaat gtatttcacc agtagcaaat gagatgaacc atcttcctgc     180
acacagccac gatttgcaaa ggttttggga gaggaataaa tttaatgaaa gatgtacatg     240
acttctaaaa actataagca gtgctgggta aaattaaaca catgatgttc acggaagacc     300
agggtgtaga tgacaggctg ctctatgaca ttgtattcaa gcacttcaaa agaaataagg     360
tggagatttc aaatgcaata aaaaagacat ttccattcct cgagggcctc cgtgatcgtg     420
atctcatcac aaataaaatg tttgaagatt ctcaagattc ttgtagaaac ctggtccctg     480
tacagagagt ggtgtacaat gttcttagtg aactggagaa gacatttaac ctgccagttc     540
tggaagcact gttcagcgat gtcaacatgc aggaataccc cgatttaatt cacatttata     600
aaggctttga aaatgtaatc catgacaaat tgcctctcca agaaagtgaa gaagaagaga     660
gggaggagag gtctggcctc caactaagtc ttgaacaagg aactggtgaa aactcttttc     720
gaagcctgac ttggccacct tcgggttccc catctcatgc tggtacaacc ccacctgaaa     780
atggactctc agagcacccc tgtgaaacag aacagataaa tgcaaagaga aagatacaa     840 ccagtgacaa agatgattcg ctaggaagcc aacaaacaaa tgaacaatgt gctcaaaagg     900
ctgagccaac agagtcctgc gaacaaattg ctgtccaagt gaataatggg gatgctggaa     960
gggagatgcc ctgcccgttg ccctgtgatg aagaaagccc agaggcagag ctacacaacc    1020
atggaatcca aattaattcc tgttctgtgc gactggtgga tataaaaaag gaaaagccat    1080
tttctaattc aaaagttgag tgccaagccc aagcaagaac tcatcataac caggcatctg    1140
acataatagt catcagcagt gaggactctg aaggatccac tgacgttgat gagcccttag    1200
aagtcttcat ctcagcaccg agaagtgagc ctgtgatcaa taatgacaac cctttagaat    1260
caaatgatga aaaggagggc caagaagcca cttgctcacg accccagatt gtaccagagc    1320
ccatggattt cagaaaatta tctacattca gagaaagttt taagaaaaga gtgataggac    1380
aagaccacga cttttcagaa tccagtgagg aggaggcgcc cgcagaagcc tcgagcgggg    1440
cactgagaag caagcatggt gagaaggctc ctatgacttc tagaagtaca tctacttgga    1500
gaatacccag caggaagaga cgtttcagca gtagtgactt tcagaccctg agtaatggag    1560
aagagcttca ggaaacctgc agctcatccc taagaagagg gtcaggtaaa aagagattagg    1620 atgccaagac ttggcctgca gaatgtcagg aatgtgaatt aaaagctgct gtttccagac    1680
gctttttatt ctgagcacct tcactacctt gtatccagtt catctgggaa ctcctttttg    1740 catttttagaa aatggaaaga ggcaggaaat tatgataaac tcatgtttaa cagaaagagt    1800
```

| | |
|---|---:|
| ttcactgact aaatgtatgt aattatattt tgttgttgta gaagaaataa atagcaaatt | 1860 |
| tgtggtattc ttttttttaa acctgctctc attcctatta acactaagat cttagatttt | 1920 |
| tatagtgata aatgggttga catcattgtc atttgtaatt gtaaagcctc aaaagacaac | 1980 |
| tgttcctact atgtaattat agacagaaat aaaaacttca gatcaaacac tctcaaacgt | 2040 |
| taaaaaaaaa | 2050 |

<210> SEQ ID NO 13
<211> LENGTH: 2223
<212> TYPE: DNA
<213> ORGANISM: Homo sapiens
<300> PUBLICATION INFORMATION:
<301> AUTHORS: Kiriakidou M., et al.
<302> TITLE: Cloning and expression of premate Daxx cDNAs...
<303> JOURNAL: DNA Cell Biol.
<304> VOLUME: 16
<305> ISSUE: 11
<306> PAGES: 1289-1298
<307> DATE: 1997-11-01
<308> DATABASE ACCESSION NUMBER: genBank/CR457085
<309> DATABASE ENTRY DATE: 2008-10-16
<313> RELEVANT RESIDUES IN SEQ ID NO: (1)..(2223)

<400> SEQUENCE: 13

| | |
|---|---:|
| atggccaccg ctaacagcat catcgtgctg gatgatgatg acgaagatga agcagctgct | 60 |
| cagccagggc cctcccaccc actccccaat gcggcctcac ctgggcaga agcccctagc | 120 |
| tcctctgagc tcatggggc cagaggaagc agtagttcgg gcggcaagaa atgctacaag | 180 |
| ctggagaatg agaagctgtt cgaagagttc cttgaacttt gtaagatgca gacagcagac | 240 |
| caccctgagg tggtcccatt cctctataac cggcagcaac gtgcccactc tctgtttttg | 300 |
| gcctcggcg agttctgcaa catcctctct agggtcctgt ctcgggcccg gagccggcca | 360 |
| gccaagctct atgtctacat caatgagctc tgcactgttc tcaaggccca ctcagccaaa | 420 |
| aagaagctga acttggcccc tgccgccacc acctccaatg agccctctgg gaataaccct | 480 |
| cccacacacc tctccttgga ccccacaaat gctgaaaaca ctgcctctca gtctccaagg | 540 |
| acccgtggtt cccggcggca gatccagcgt ttggagcagc tgctggcgct ctatgtggca | 600 |
| gagatccggc ggctgcagga aaaggagttg gatctctcag aattggatga cccagactcc | 660 |
| gcatacctgc aggaggcacg gttgaagcgt aagctgatcc gcctctttgg gcgactatgt | 720 |
| gagctgaaag actgctcttc actgaccggc cgtgtcatag agcagcgcat ccctaccgt | 780 |
| ggcacccgct acccagaggt taacaggcgc attgagcggc tcatcaacaa gccagggcct | 840 |
| gataccttcc ctgactatgg ggatgtgctt cgggctgtag agaaggcagc tgcccgacac | 900 |
| agccttggcc tcccccgaca gcagctccag ctcatggctc aggatgcctt ccgagatgtg | 960 |
| ggcatcaggt tacaggagcg acgtcacctc gatctcatct acaactttgg ctgccacctc | 1020 |
| acagatgact ataggccagg cgttgaccct gcactatcag atcctgtgtt ggcccggcgc | 1080 |
| cttcgggaaa accggagttt ggccatgagt cggctggatg aggtcatctc caaatatgca | 1140 |
| atgttgcaag acaaaagtga ggagggcgag agaaaaaaga gaagagctcg gctccaaggc | 1200 |
| acctcttccc actctgcaga caccccccgaa gcctccttgg attctggtga gggccctagt | 1260 |
| ggaatggcat cccagggggtg cccttctgcc tccagagctg agacagatga cgaagacgat | 1320 |
| gaggagagtg atgaggaaga ggaggaggag gaggaagaag aagaggagga ggccacagat | 1380 |
| tctgaagagg aggaggatct ggaacagatg caggagggtc aggaggatga tgaagaggag | 1440 |
| gacgaagagg aagaagcagc agcaggtaaa gatggagaca agagccccat gtcctcacta | 1500 |

-continued

```
cagatctcca atgaaaagaa cctggaacct ggcaaacaga tcagcagatc ttcaggggag    1560
cagcaaaaca aaggacgcat agtgtcacca tcgttactgt cagaagaacc cctggccccc    1620
tccagcatag atgctgaaag caatggagaa cagcctgagg agctgaccct ggaggaagaa    1680
agccctgtgt ctcagctctt tgagctagag attgaagctt tgcccctgga tacccccttcc   1740 tctgtggaga cggacatttc ctcttccagg aagcaatcag aggagcccct caccactgtc    1800
ttagagaatg gagcaggcat ggtctcttct acttccttca atggaggcgt ctctcctcac    1860
aactggggag attctggtcc cccctgcaaa aaatctcgga aggagaagaa gcaaacagga    1920
tcagggccat taggaaacag ctatgtggaa aggcaaaggt cagtgcatga aagaatgggg    1980
aaaaagatat gtaccctgcc cagcccacct tcccccttgg cttccttggc cccagttgct    2040
gattcctcca cgagggtgga ctctcccagc catggcctgg tgaccagctc cctctgcatc    2100
ccttctccag cccggctgtc ccaaaccccc cattcacagc ctcctcggcc tggtacttgc    2160
aagacaagtg tggccacaca atgcgatcca aagagatca tcgtgctctc agactctgat    2220
taa                                                                  2223
```

<210> SEQ ID NO 14
<211> LENGTH: 2251
<212> TYPE: DNA
<213> ORGANISM: Homo sapiens
<300> PUBLICATION INFORMATION:
<301> AUTHORS: H de The, et al.
<302> TITLE: The PML-RAR alpha fusion mRNA generated by the t(15;17) translocation...
<303> JOURNAL: Cell
<304> VOLUME: 66
<305> ISSUE: 4
<306> PAGES: 675-684
<307> DATE: 1991-08-23
<308> DATABASE ACCESSION NUMBER: genBank/S50913
<309> DATABASE ENTRY DATE: 2000-06-29
<313> RELEVANT RESIDUES IN SEQ ID NO: (1)..(2251)

<400> SEQUENCE: 14

```
gccaactggc tcacgcctcc ccttcagctt ctcttcacgc actccaagat ctaaaccgag     60
aatcgaaact aagctggggt ccatggagcc tgcacccgcc cgatctccga ggccccagca   120
ggaccccgcc cggccccagg agcccaccat gcctccccccc gagacccct ctgaaggccg    180 ccagcccagc cccagcccca gccctacaga gcgagccccc gcttcggagg aggagttcca   240
gtttctgcgc tgccagcaat gccaggcgga agccaagtgc ccgaagctgc tgccttgtct   300
gcacacgctg tgctcaggat gcctggaggc gtcgggcatg cagtgcccca tctgccaggc   360
gccctggccc ctaggtgcag acacacccgc cctggataac gtcttttttcg agagtctgca   420 gcggcgcctg tcggtgtacc ggcagattgt ggatgcgcag gctgtgtgca cccgctgcaa   480
agagtcggcc gacttctggg ctttgagtg cgagcagctc ctctgcgcca agtgcttcga    540
ggcacaccag tggttcctca agcacgaggc ccggccccta gcagagctgc gcaaccagtc    600
ggtgcgtgag ttcctggacg gcacccgcaa gaccaacaac atcttctgct ccaaccccaa    660
ccaccgcacc cctacgctga ccagcatcta ctgccgagga tgttccaagc cgctgtgctg    720
ctcgtgcgcg ctccttgaca gcagccacag tgagctcaag tgcgacatca gcgcagagat    780
ccagcagcga caggaggagc tggacgccat gacgcaggcg ctgcaggagc aggatagtgc    840
ctttggcgcg gttcacgcgc agatgcacgc ggccgtcggc cagctgggcc gcgcgcgtgc    900
cgagaccgag gagctgatcc gcgagcgcgt gcgccaggtg gtagctcacg tgcgggctca    960
```

```
ggagcgcgag ctgctggagg ctgtggacgc gcggtaccag cgcgactacg aggagatggc      1020
cagtcggctg ggccgcctgg atgctgtgct gcagcgcatc cgcacgggca gcgcgctggt      1080
gcagaggatg aagtgctacg cctcggacca ggaggtgctg gacatgcacg gtttcctgcg      1140
ccaggcgctc tgccgcctgc gccaggagga gccccagagc ctgcaagctg ccgtgcgcac      1200
cgatggcttc gacgagttca aggtgcgcct gcaggacctc agctcttgca tcacccaggg      1260
gaaagatgca gctgtatcca agaaagccag cccagaggct gccagcactc cagggaccc      1320 tattgacgtt gacctgcccg aggaggcaga gagagtgaag gcccaggttc aggccctggg      1380
gctggctgaa gcccagccta tggctgtggt acagtcagtg cccggggcac acccgtgcc       1440 agtgtacgcc ttctccatca aaggcccttc ctatggagag gatgtctcca atacaacgac      1500
agcccagaag aggaagtgca gccagaccca gtgcccagg aaggtcatca agatggagtc       1560
tgaggagggg aaggaggcaa ggttggctcg gagctccccg gagcagccca ggcccagcac      1620
ctccaaggca gtctcaccac cccacctgga tggaccgcct agcccagga gccccgtcat       1680 aggaagtgag gtcttcctgc caacagcaa ccacgtggcc agtggcgccg gggaggcaga      1740
ggaacgcgtt gtggtgatca gcagctcgga agactcagat gccgaaaact cggtctcttc      1800
cagccctcag tctgaggttc tgtattggaa agtgcatgga gcccatggag accgccgagc      1860
cacagtcctc gccagcccac tcctcgccag cccactcctc gccagcccac tcctcgccag      1920
tccagtctct gctgagagca caaggagcct ccagcctgcc ctgtggcaca taccaccccc      1980
cagcttggcc tccccaccag cccgctgagc aggctgccac ccccgatgct gagcctcaca      2040
gcgagcctcc tgatcaccag gagcgccctg ccgtccaccg tgggatccgc tacctgttgt      2100
acagagcaca gagagccatc cgccttcgcc atgccctccg cttgcaccct caattgcatc      2160
gggcccctat tcggacttgg tctccccatg tggtccaagc cagcactcct gccatcacag      2220
ggcccctcaa ccatcctgcc aatgcccagg a                                    2251
```

<210> SEQ ID NO 15
<211> LENGTH: 4373
<212> TYPE: DNA
<213> ORGANISM: Homo sapiens
<300> PUBLICATION INFORMATION:
<301> AUTHORS: Mammalian Gene Collection Program Team.
<302> TITLE: Generation and initial analysis of more than 15,000 full-length human...
<303> JOURNAL: Proc. Natl. Acad. Sci. U.S.A.
<304> VOLUME: 99
<305> ISSUE: 26
<306> PAGES: 16899-16903
<307> DATE: 2002-12-24
<308> DATABASE ACCESSION NUMBER: genBank/BC144281
<309> DATABASE ENTRY DATE: 2009-01-08
<313> RELEVANT RESIDUES IN SEQ ID NO: (1)..(4373)

<400> SEQUENCE: 15

```
ttcctcgcgt tcttgagtcg ggaaatggcc gctgtgtggt tgcaacggag ataaattccc        60
ggaaccgcga ttcggcgtgt caggaattcg aatttagagt ttaatttctc agagcattct       120
ctccaggaag aatttttaca gtatctcaaa gacttcactt gacttcttga tcctgcataa       180
aaccaaggag aaaagaaatg ggtcgctcca attctagatc acattcttca aggtcaaagt       240
ctagatcaca gtctagttct cgatcaagat caagatctca ttctagaaag aagcgataca       300
ggtctcgttc cagaacatat tcaaggtctc gtagtagaga tcgtatgtat tctagagatt       360
atcgtcgcga ttacagaaat aatagaggaa tgagacgacc ttatgggtac agaggaaggg      420
gtagagggta ttatcaagga ggaggaggta gatatcatcg aggtggttat agacctgtct      480
```

```
ggaatagaag gcactctagg agtcctagac gaggtcgttc acgttccagg agtccaaaaa    540
gaagatccgt ttcttctcaa agatccgaaa gcagatctcg ccggtcatat agatcttcta    600
ggtctccaag atcatcctct tctcgttctt catccccata tagcaaatct cctgtttcta    660
aaagacgagg gtctcaggaa aaacaaacca aaaaagctga aggggaaccc caagaagaga    720
gtccgttgaa aagtaaatca caggaggaac cgaaagatac atttgaacat gacccatctg    780
agtctatcga tgaatttaat aagtcatcag ccacatccgg tgatatttgg cctggccttt    840
cagcttatga taatagtcct agatcacccc atagtccttc acctattgct acaccaccta    900
gtcagagttc atcttgctct gatgctccca tgctcagtac agttcactct gcaaaaaata    960
ctccttctca gcattcacat tccattcagc atagtcctga aggtctgggt tctggttctg   1020
ttggaaatgg atctagtcga tacagtcctt ctcagaatag tccaattcat cacatcccct   1080
cacgaagaag tcctgcaaag acaatcgcac cacagaatgc tccaagagat gagtctaggg   1140
gccgttcctc gttttatcct gatggtggag atcaggaaac tgcaaagact gggaagttct   1200
taaaaaggtt cacagatgaa gagtctagag tattcctgct tgatagggt aataccaggg    1260
ataaagaggc ttcaaaagag aaaggatcag agaaagggag ggcagaggga gaatgggaag   1320
atcaggaagc tctagattac ttcagtgata aagagtctgg aaaacaaaag tttaatgatt   1380
cagaagggga tgacacagag gagacagagg attatagaca gttcaggaag tcagtcctcg   1440
cagatcaggg taaaagtttt gctactgcat ctcaccggaa tactgaggag gaaggactca   1500
agtacaagtc caaagtttca ctgaaaggca atagagaaag tgatggattt agagaagaaa   1560
aaaattataa acttaaagag actggatatg tagtggaaag gcctagcact acaaaagata   1620
agcacaaaga agaagacaaa aattctgaaa gaataacagt aaagaaagaa actcagtcac   1680
ctgagcaggt aaagtctgaa aagctcaaag acctctttga ttacagtccc cctctacaca   1740
agaatctgga tgcacgagaa aagtctacct tcagagagga aagcccactt aggatcaaaa   1800
tgatagcgag tgattctcac cgtcctgaag tcaaactcaa aatggcacct gttcctcttg   1860
atgattctaa cagacctgct tccttgacta aagacaggct gcttgctagt acacttgtcc   1920
attctgtcaa gaaggagcaa gaattccgat ccatctttga ccacattaag ttgccacagg   1980
ccagcaaaag cacttcagag tcatttattc aacacattgt gtccttggtt catcatgtta   2040
aagagcaata cttcaagtca gctgcaatga ccctaaacga gcggttcact tcgtatcaga   2100
aagccactga agaacatagt actcggcaaa agagccctga atacacagg agaattgaca    2160
tctcaccaag taccctgagg aagcataccc gtttagcagg ggaagagaga gtttttaaag   2220
aagaaaatca aaagggagat aaaaaattaa ggtgtgactc tgctgacctt cggcatgaca   2280
ttgatcgccg tagaaaagaa agaagtaaag aacggggaga ttccaagggc tccagggaat   2340
ccagtggatc aagaaagcag gaaaaaactc caaaagatta caaggaatac aaatcttaca   2400
aagatgacag taaacataaa agagagcaag atcattctcg atcttcatcc tcttcagcat   2460
caccttcttc tcccagttct cgagaagaaa aggagagtaa aaggaaaga gaagaagaat    2520
ttaaaactca ccatgaaatg aaagaatact caggctttgc aggagttagc cgaccacgag   2580
gaaccttttt tcgaattaga ggcagaggaa gagccagagag agtttttgct gggacaaata   2640
ctggtccaaa caactcaaat actacttttc aaaagagacc gaaggaagag gaatgggatc   2700
cagaatatac cccaaagagc aagaagtact tcttgcatga cgacagagat gatggtgtgg   2760
attattgggc caaaagagga agaggtcgtg gtacttttca acgtggcaga gggcgcttta   2820
```

| | |
|---|---:|
| acttcaaaaa atcaggtagc agtcctaaat ggactcatga caaataccaa ggggatggga | 2880 |
| ttgttgaaga tgaagaagag accatggaaa ataatgaaga aagaaggac agacgcaagg | 2940 |
| aagaaaagga ataataaata tgaagtaaga ttacaacaga gcagaacttg cacccaccat | 3000 |
| tttttttacc tgattttgt tttcaaataa gaatgtaagc attttactta aattttactg | 3060 |
| tttgcaagta gtctatagaa attttgtttt aagtcttcaa atatcttgag aaatagtaga | 3120 |
| ctgtatgttg aaaattgtac tgaaataaag tagaaaattg ttacgtacca tatttgtaac | 3180 |
| tatcaacttt taaaactttt aacgtttttg ttacatgcat tgtaattctg ctttgtctat | 3240 |
| aagatatggt caagtacagc tctgtgaaag ttctgattct cttccttccc tgtttgtcaa | 3300 |
| tgttttattc tgaagtaaac gttagctcta catataaatc ctggaacaga aattgtttat | 3360 |
| agagactaca ctaattattt taactgtata catctgttta atttgaacac actacatcgt | 3420 |
| agggtgactg attttgaag tataccacag acaaaaagtt gttactatgg taaactaagc | 3480 |
| tagtttaaca cttgagcaaa tgcttaagaa ggaattaaaa aaaaaaagct ttgccaatag | 3540 |
| ctaaaaagta caagctatta aaaatcagat tgaaaagttt tgagaaaatg ttattttac | 3600 |
| tgaaagcaag cagtggccta taaagaacat tcttaggagc cttttctatt tgcgttcaaa | 3660 |
| actgtgtgtt ctctttctat tcctatttga tagtttgagt catggtctta gatattagct | 3720 |
| atttgtgaga ggaaactggt ttgtaacaat actgcaaata gaaacccat ttctactgaa | 3780 |
| catcctagtt ttaaacagaa gaaaaactgt aatcctgggg ttggtatgta ggaggtctat | 3840 |
| cctgcagaat aagttgatac attagtacct gatttcatat cttacatatt tatttgagct | 3900 |
| gaacattagt ttgtagtgta actattagta aaaatagaga aacacagcat actgttcatt | 3960 |
| aatagtattt taaaaaaatt gttttcaaa tgtcaccaat aaaagttttg gcaggaagct | 4020 |
| tgttgcggca ttgatctaac cttttttcccc cccatttcag ttgcagtttt tgtagaatgg | 4080 |
| cttttttcttt ttcctcttaa gagttctatt cttcaggtag ataattttc aaatgtgaat | 4140 |
| tatcttttgt gtctatattg atagctctta aaggagtgaa aatctaaaat agtaaatttc | 4200 |
| aatgttaagt gtctgcttta tgggcatata taaaagtaga cacatttcat ttgttaattt | 4260 |
| agttgtgtgt gtgtgttaaa aggagctaat gcttattctg ttaatgtaaa cttttgaaga | 4320 |
| tcttaagtgt attgctcttt catcttaaac actttcgagg atttgcagtg cgt | 4373 |

<210> SEQ ID NO 16
<211> LENGTH: 1001
<212> TYPE: DNA
<213> ORGANISM: Homo sapiens
<300> PUBLICATION INFORMATION:
<301> AUTHORS: Ishikawa J., et al.
<302> TITLE: Molecular cloning and chromosomal mapping of a bone
       marrow...
<303> JOURNAL: Genomics 1995 Apr;26(3)527-534
<304> VOLUME: 26
<305> ISSUE: 3
<306> PAGES: 527-534
<307> DATE: 1995-04-26
<308> DATABASE ACCESSION NUMBER: genBank/NM_004335
<309> DATABASE ENTRY DATE: 2002-07-13
<313> RELEVANT RESIDUES IN SEQ ID NO: (1)..(1001)

<400> SEQUENCE: 16

| | |
|---|---:|
| gaagattcca gcaccctccc ctaactccag gccagactct aaaggggaga tctggatggc | 60 |
| atctacttcg tatgactatt gcagagtgcc catggaagac ggggataagc gctgtaagct | 120 |
| tctgctgggg ataggaattc tggtgctcct gatcatcgtg attctggggg tgcccttgat | 180 |
| tatcttcacc atcaaggcca acagcgaggc ctgccgggac ggccttcggg cagtgatgga | 240 |

```
gtgtcgcaat gtcacccatc tcctgcaaca agagctgacc gaggcccaga agggctttca    300
ggatgtggag gcccaggccg ccacctgcaa ccacactgtg atggccctaa tggcttccct    360
ggatgcagag aaggcccaag gacaaaagaa agtggaggag cttgagggag agatcactac    420
attaaaccat aagcttcagg acgcgtctgc agaggtggga cgactgagaa gagaaaacca    480
ggtcttaagc gtgagaatcg cggacaagaa gtactacccc agctcccagg actccagctc    540
cgctgcggcg ccccagctgc tgattgtgct gctgggcctc agcgctctgc tgcagtgaga    600
tcccaggaag ctggcacatc ttggaaggtc cgtcctgctc ggcttttcgc ttgaacattc    660
ccttgatctc atcagttctg agcgggtcat ggggcaacac ggttagcggg gagagcacgg    720
ggtagccgga gaagggcctc tggagcaggt ctggaggggc catgggaag tcctgggtgt     780 ggggacacag tcgggttgac ccagggctgt ctccctccag agcctccctc cggacaatga    840 gtccccctc ttgtctccca ccctgagatt gggcatgggg tgcggtgtgg ggggcatgtg     900
ctgcctgttg ttatgggttt ttttgcgggg ggggttgct tttttctggg gtctttgagc     960
tccaaaaaat aaacacttcc tttgagggag agcacacctg a                         1001
```

<210> SEQ ID NO 17
<211> LENGTH: 3364
<212> TYPE: DNA
<213> ORGANISM: Homo sapiens
<300> PUBLICATION INFORMATION:
<301> AUTHORS: Scherer, Myriam et al.
<302> TITLE: Crystal Structure of CMV IE1 Protein Reveals Targeting of
    TRIM Family...
<303> JOURNAL: PLoS Pathog
<304> VOLUME: 10
<305> ISSUE: 11
<306> PAGES: e1004512
<307> DATE: 2014-11-14
<308> DATABASE ACCESSION NUMBER: genBank/NM_033034
<309> DATABASE ENTRY DATE: 2002-05-14
<313> RELEVANT RESIDUES IN SEQ ID NO: (1)..(3364)

<400> SEQUENCE: 17

```
aagaatttcc tgcggttcct ctaggaaaat tcctttgtgc agatcaggcc cgtggattgg     60
tgagtgaatc ctaaccacgt cttccctggc ctgtcttcac tcttctcccc agaatcacca    120
cttctgcact ggtgtctgaa ggtgtattga gtgattttgt ggagggcaga agtaggaagt    180 cttgtgggaca aaactgtatt taccttggga tctgtgaaca agaggaacct cagcagccag    240
gacaggcagg agcagtggaa tagctactat ggcttctgga atcctggtta atgtaaagga    300
ggaggtgacc tgccccatct gcctggaact cctgacacaa cccctgagcc tggactgcgg    360
ccacagcttc tgccaagcat gcctcactgc aaaccacaag aagtccatgc tagacaaagg    420
agagagtagc tgccctgtgt gccggatcag ttaccagcct gagaacatac ggcctaatcg    480
gcatgtagcc aacatagtgg agaagctcag ggaggtcaag ttgagcccag aggggcagaa    540
agttgatcat tgtgcacgcc atggagagaa acttctactc ttctgtcagg aggacgggaa    600
ggtcatttgc tggctttgtg agcggtctca ggagcaccgt ggtcaccaca cgttcctcac    660
agaggaggtt gcccgggagt accaagtgaa gctccaggca gctctggaga tgctgaggca    720
gaagcagcag gaagctgaag agttagaagc tgacatcaga gaagagaaag cttcctggaa    780
gactcaaata cagtatgaca aaaccaacgt cttggcagat tttgagcaac tgagagacat    840
cctggactgg gaggagagca atgagctgca aaacctggag aaggaggagg aagcattct     900 gaaaagcctt acgaactctg aaactgagat ggtgcagcag acccagtccc tgagagagct    960
```

-continued

```
catctcagat ctggagcatc ggctgcaggg gtcagtgatg gagctgcttc agggtgtgga    1020
tggcgtcata aaaaggacgg agaacgtgac cttgaagaag ccagaaactt ttccaaaaaa    1080
tcaaaggaga gtgtttcgag ctcctgatct gaaaggaatg ctagaagtgt ttagagagct    1140
gacagatgtc cgacgctact gggttgatgt gacagtggct ccaaacaaca tttcatgtgc    1200
tgtcatttct gaagataaga gacaagtgag ctctccgaaa ccacagataa tatatggggc    1260
acgagggaca agataccaga catttgtgaa tttcaattat tgtactggca tcctgggctc    1320
tcaaagtatc acatcaggga acattactg ggaggtagac gtgtccaaga aaactgcttg    1380
gatcctgggg gtatgtgctg gcttccaacc tgatgcaatg tgtaatattg aaaaaaatga    1440
aaattatcaa cctaaatacg gctactgggt tatagggtta gaggaaggag ttaaatgtag    1500
tgctttccag gatagttcct tccatactcc ttctgttcct ttcattgtgc ccctctctgt    1560
gattatttgt cctgatcgtg ttggagtttt cctagactat gaggcttgca ctgtctcatt    1620
cttcaatatc acaaccatg gatttctcat ctataagttt tctcactgtt cttttttctca    1680 gcctgtattt ccatatttaa atcctagaaa atgtggagtc cccatgactc tgtgctcacc    1740
aagctcttga accttcttac acactcagcc ccttctgtac agcacctctt gtccaggtgc    1800
atctcataca cctgaactca tttgcatcat tttaaccatc ttttccttgc tgtctccctt    1860
cttctctttt gaacgtcctt cactcatcag taaaatgtaa taattgcctt gtgccatatt    1920
gtccccaata ttttattgac atttgatagc aattttttc atcatttttcc gtactcctaa    1980 ggaaaactga cctatacctc ataaaatgag accgctattt aggtattact tctgccagat    2040
atttatcacc caattgcctc tgacactgac taagaagatg aagaaaagct ttcaacagc    2100 ctttctatat catcgtgtga taattgttca ccaatgaatg agtccttagc cctgtgtcag    2160
tttaccctcg atgcccttat ttgtgagtta agagaaaaat atcataaatg gtatactctt    2220
aagtatagag gttttgtatc tagaggatct cagttcaact cctgtctctc catataccag    2280
cagtgtaact gtgaataaca tacttaaatg gctgtgctta tttcctttc ttttcttttt    2340 tctttttttt ttttttgag atgaagtttt gctcttgttc cccaggctgg agtgcaatgg    2400
cacgatctcg gttcactgca acctccacct ctcagattca agcaattctc ctgcctcagc    2460
ctcccaagta gctgggatta caggtgccca ccaccaccc tggctaaatt tgtattttca    2520
gtagagacgg ggtttcccca tgttggttag gctcgtctag aacctctgac ctcaggtgat    2580
ccacccgcct cggcctccca agtgctggga ttacaggcg tgagccacgg cgcccagcct    2640
gtgcttattt tcttaaaata atttttgtat taaaaacttc acattaaata agtgctaatg    2700
ttttattgca tagtagggtg actagagtta acaataacct attgcatata ttttgaaata    2760
gctagaagag aggattttga aagttctcaa cacaaagaaa tgacacatat ttgaggtgat    2820
ggatatgcta attaccctgg ttcggttatt acgcaatgta tacatgtatc aaaacatcac    2880
actgtaccac ataaatatgt atatttatta tttgtcaatt aaaagcaaaa taaaacaaaa    2940
aaccttcatc taatactttg gatcattgtg aaaaaataaa ttcctgaagt ataaagcatc    3000
tatctaagtg tcttgatcta ataagtactt gttctacaaa ttattgaaaa acataaactc    3060
tgttaatgtc tcatggaaca ggttgtgcct tcagggaaac taggattgga tttactaaat    3120
tctcattttt tagatctcag atactactgt caaaatgact tcaattctgc cttctatata    3180
taatacacac atatatttag gatttttattg taattctagt gttgctacat attagtcttt    3240
atcaaacaaa ctgaattatg tgggaatcag tttattaatt gtaaaaaata attataataa    3300
aattagctga tgtagttttt taaaagttaa acgagttttt tgaatagctt cactcatttc    3360
``` tagc                                                                    3364

<210> SEQ ID NO 18
<211> LENGTH: 2299
<212> TYPE: DNA
<213> ORGANISM: Homo sapiens
<300> PUBLICATION INFORMATION:
<301> AUTHORS: Li J., Potash M.J. and Volsky D.J.
<302> TITLE: Functional domains of APOBEC3G required for antiviral
       activity
<303> JOURNAL: J. Cell. Biochem.
<304> VOLUME: 92
<305> ISSUE: 3
<306> PAGES: 560-572
<307> DATE: 2004-06-01
<308> DATABASE ACCESSION NUMBER: genBank/NM_001349438
<309> DATABASE ENTRY DATE: 2012-12-13
<313> RELEVANT RESIDUES IN SEQ ID NO: (1)..(2299)

<400> SEQUENCE: 18
gggctgtcct aaaaccagaa gcttggagca gaaagtgaaa ccctggtgct ccagacaaag      60
atcttagtcg ggactagccg gccaaggatg aagcctcact tcagaaacac agtggagcga     120
atgtatcgag acacattctc ctacaacttt tataatagac ccatcctttc tcgtcggaat     180
accgtctggc tgtgctacga agtgaaaaca aagggtccct caaggccccc tttggacgca     240
aagatctttc gaggccaggt gtattccgaa cttaagtacc acccagagat gagattcttc     300
cactggttca gcaagtggag gaagctgcat cgtgaccagg agtatgaggt cacctggtac     360
atatcctgga gccctgcac aaagtgtaca agggatatgg ccacgttcct ggccgaggac     420
ccgaaggtta ccctgaccat ctttgttgcc cgcctctact acttctggga cccagattac     480
caggaggcgc ttcgcagcct gtgtcagaaa agagacggtc cgcgtgccac catgaagatc     540
atgaattatg acgaatttca gcactgttgg agcaagttcg tgtacagcca aagagagcta     600
tttgagcctt ggaataatct gcctaaatat tatatattac tgcacatcat gctggggag      660 attctcaggt gagggtctcc ctccaggctc atcgcctcgc tcctctcacc tcctgctcat     720
cctcttgagg cctcccctct gttccagacc aggtcctctc ctggccaggc cctcctgcct     780
tccctcctgc cccctgcctg ccctcgtggt tacactccct cacccacact cctcgtgctc     840
cctccacctc cctgcctccc acctgctttc ctgggcccct tcctgtgagtg agaggcccct     900 tctgcctcca gagcaacctc catccacccc cacagcctgg gagccccaac ctggcccctt     960
ccatctccct ggcataaccg aatttgtcgt aaaactggac gtagtaagtg gcatgaata     1020 gtcacaagcc cggcagtcag aagctttgag caacatcctt aaaggccaac ctgagccct     1080 gagaaggagc tgcctccatg gaaacagagc ttcaggcttc ggctgccata agatggcc      1140 gggctgggtg cccacagggc aggcatttat tttctcacac atctggaggc tgcaagtcca    1200
aggtggaggg gtgggcgggg ttgtgtcttc tgcagtcgct cctcctggct ggcaggggt     1260 cccttccggc cctgtcctct ctggcctttc tctgtgcac ctgcactcgt ggggtctctc     1320
tgcctccaaa tgtcctcctc gtttatggac cccagtcatg tgaatttggg cccacactga    1380
aggtctcatt taagttaatc atctgatgaa aggacctgtc tccaggccag gtgcagaggc    1440
tcatgcctgt aatcccagca ctttgggagt ccaaggcggg tggatcacct gaggtcagga    1500
gttcgacacc agcctggcca acatgttaaa accccatctc taccaaaaat acaaaaatta    1560
gccgggagtg gtggtgggcg cctataattc tagctactcg gaaggctgag gcaggagaat    1620
cgcttgaacc cgggaggcgg aggttgcggt gagcccagac tgcgccgctg cactccagcc    1680

| | | | |
|---|---|---|---|
| tgggcaaaaa | agcgaaactt | cttcctcaaac aaacaaacaa gaaagaaagg acctgtttcc | 1740 |
| aaatacagcc | acccttttgag | ggagcggggg ttaaggcttc aatacattga ttttggggag | 1800 |
| aaacagtgaa | ggccacggca | agaagctgca gtcattgtgg gcgggcctgg gtggggagtg | 1860 |
| caggggttcc | tgtcctgtgt | gtctgttttcc caggggagtc ctgacctgac tctcacagcc | 1920 |
| cctccaccca | gatgttcctg | tgtgcttcac ccaccccatt ccttctgcac ccaacactcc | 1980 |
| tgagcccctc | cttagctccc | ccgacaggct cccctgctcc cccactcccg ggctgctcct | 2040 |
| cttctcagcc | tctctctggg | cctctctggg gtccggacat gacccctcag ctgatgcctg | 2100 |
| tggcttcccc | agccagaatc | ttcccagttc caggctgggc tctgcagagt cctatcaaag | 2160 |
| gtggcatcct | cccctctgtc | cactccaggg tgaagatctg gtgtttctgg tttggaaatg | 2220 |
| cctctgcact | gggtgctaat | aattcacttt tacctttata attgtggttt tgtaaggaca | 2280 |
| ggtattttg gcaacagaa | | | 2299 |

<210> SEQ ID NO 19
<211> LENGTH: 1166
<212> TYPE: DNA
<213> ORGANISM: Homo sapiens
<300> PUBLICATION INFORMATION:
<301> AUTHORS: McLean, J.W. et al.
<302> TITLE: Human apolipoprotein E mRNA cDNA cloning...
<303> JOURNAL: J. Biol. Chem.
<304> VOLUME: 259
<305> ISSUE: 10
<306> PAGES: 6498-6504
<307> DATE: 1984-05-25
<308> DATABASE ACCESSION NUMBER: geneBank/NM_000041
<309> DATABASE ENTRY DATE: 2006-07-15
<313> RELEVANT RESIDUES IN SEQ ID NO: (1)..(1166)

<400> SEQUENCE: 19

| | | | |
|---|---|---|---|
| ctactcagcc | ccagcggagg | tgaaggacgt ccttccccag gagccgactg ccaatcaca | 60 |
| ggcaggaaga | tgaaggttct | gtgggctgcg ttgctggtca cattcctggc aggatgccag | 120 |
| gccaaggtgg | agcaagcggt | ggagacagag ccggagcccg agctgcgcca gcagaccgag | 180 |
| tggcagagcg | gccagcgctg | ggaactggca ctgggtcgct tttgggatta cctgcgctgg | 240 |
| gtgcagacac | tgtctgagca | ggtgcaggag gagctgctca gctcccaggt cacccaggaa | 300 |
| ctgagggcgc | tgatggacga | gaccatgaag gagttgaagg cctacaaatc ggaactggag | 360 |
| gaacaactga | ccccggtggc | ggaggagacg cgggcacggc tgtccaagga gctgcaggcg | 420 |
| gcgcaggccc | ggctgggcgc | ggacatggag gacgtgtgcg gccgcctggt gcagtaccgc | 480 |
| ggcgaggtgc | aggccatgct | cggccagagc accgaggagc tgcgggtgcg cctcgcctcc | 540 |
| cacctgcgca | agctgcgtaa | gcggctcctc cgcgatgccg atgacctgca gaagcgcctg | 600 |
| gcagtgtacc | aggccgggc | ccgcgagggc gccgagcgcg gcctcagcgc catccgcgag | 660 |
| cgcctggggc | cctggtgga | acagggccgc gtgcgggccg ccactgtggg ctccctggcc | 720 |
| ggccagccgc | tacaggagcg | ggcccaggcc tgggcgagc ggctgcgcgc gcggatggag | 780 |
| gagatgggca | gccggacccg | cgaccgcctg gacgaggtga aggagcaggt ggcggaggtg | 840 |
| cgcgccaagc | tggaggagca | ggcccagcag atacgcctgc aggccgaggc cttccaggcc | 900 |
| cgcctcaaga | gctggttcga | gcccctggtg gaagacatgc agcgccagtg gccgggctg | 960 |
| gtggagaagg | tgcaggctgc | cgtgggcacc agcgccgcc ctgtgcccag cgacaatcac | 1020 |
| tgaacgccga | agcctgcagc | catgcgaccc cacgccaccc cgtgcctcct gcctccgcgc | 1080 |
| agcctgcagc | gggagaccct | gtccccgccc cagccgtcct cctggggtgg acctagtttt | 1140 | aataaagatt caccaagttt cacgca                                        1166

<210> SEQ ID NO 20
<211> LENGTH: 1144
<212> TYPE: DNA
<213> ORGANISM: Homo sapiens
<300> PUBLICATION INFORMATION:
<301> AUTHORS: Arboleda-Velasquez, et al.
<302> TITLE: Resistance to autosomal dominant Alzheimer's Disease...
<303> JOURNAL: Nature Medicine
<304> VOLUME: 25
<305> ISSUE: 11
<306> PAGES: 1680-1683
<307> DATE: 2019-11-01
<308> DATABASE ACCESSION NUMBER: genBank/NM_001302689
<309> DATABASE ENTRY DATE: 2006-07-15
<313> RELEVANT RESIDUES IN SEQ ID NO: (1)..(1144)

<400> SEQUENCE: 20
agagacgacc cgacccgcta aagactggc caatcacagg caggaagatg aaggttctgt      60
gggctgcgtt gctggtcaca ttcctggcag gatgccaggc caaggtggag caagcggtgg    120
agacagagcc ggagcccgag ctgcgccagc agaccgagtg gcagagcggc cagcgctggg    180
aactggcact gggtcgcttt tgggattacc tgcgctgggt gcagacactg tctgagcagg    240
tgcaggagga gctgctcagc tcccaggtca cccaggaact gagggcgctg atggacgaga    300
ccatgaagga gttgaaggcc tacaaatcgg aactggagga acaactgacc ccggtggcgg    360
aggagacgcg ggcacggctg tccaaggagc tgcaggcggc gcaggcccgg ctgggcgcgg    420
acatggagga cgtgtgcggc cgcctggtgc agtacagcgg cgaggtgcag gccatgctcg    480
gccagagcac cgaggagctg cgggtgcgcc tcgcctccca cctgcgcaag ctgcgtaagc    540
ggctcctccg cgatgccgat gacctgcaga agcgcctggc agtgtaccag gccgggcccc    600
gcgagggcgc cgagcgcggc ctcagcgcca tccgcgagcg cctggggccc ctggtggaac    660
agggccgcgt gcgggccgcc actgtgggct ccctggccgg ccagccgcta caggagcggg    720
cccaggcctg gggcgagcgg ctgcgcgcgc ggatggagga gatgggcagc cggacccgcg    780
accgcctgga cgaggtgaag gagcaggtgg cggaggtgcg cgccaagctg gaggagcagg    840
cccagcagat acgcctgcag gccgaggcct tccaggcccg cctcaagagc tggttcgagc    900
ccctggtgga agacatgcag cgccagtggg ccgggctggt ggagaaggtg caggctgccg    960
tgggcaccag cgccgcccct gtgcccagcg acaatcactg aacgccgaag cctgcagcca   1020
tgcgacccca cgccaccccg tgcctcctgc ctccgcgcag cctgcagcgg gagaccctgt   1080
ccccgcccca gccgtcctcc tggggtggac cctagtttaa taaagattca ccaagtttca   1140
cgca                                                                1144

<210> SEQ ID NO 21
<211> LENGTH: 21
<212> TYPE: DNA
<213> ORGANISM: Human cytomegalovirus
<220> FEATURE:
<221> NAME/KEY: Synthetic
<222> LOCATION: (1)..(21)
<223> OTHER INFORMATION: BLOCK-iT? RNAi Designer
<300> PUBLICATION INFORMATION:
<308> DATABASE ACCESSION NUMBER: GenBanK: NC_006273.2
<309> DATABASE ENTRY DATE: 2023-08-18
<313> RELEVANT RESIDUES IN SEQ ID NO: (1)..(21)

<400> SEQUENCE: 21
gcaagatctc gcacatcatg c                                               21

```
<210> SEQ ID NO 22
<211> LENGTH: 21
<212> TYPE: DNA
<213> ORGANISM: Human cytomegalovirus
<220> FEATURE:
<221> NAME/KEY: synthetic
<222> LOCATION: (1)..(21)
<223> OTHER INFORMATION: BLOCK-iT? RNAi Designer
<300> PUBLICATION INFORMATION:
<308> DATABASE ACCESSION NUMBER: GenBank: NC_006273.2
<309> DATABASE ENTRY DATE: 2023-11-20
<313> RELEVANT RESIDUES IN SEQ ID NO: (1)..(21)

<400> SEQUENCE: 22
gcgcatgtcc agtctgttta a                                                   21

<210> SEQ ID NO 23
<211> LENGTH: 102
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000454
<309> DATABASE ENTRY DATE: 2018-10-01
<313> RELEVANT RESIDUES IN SEQ ID NO: (59)..(82)

<400> SEQUENCE: 23
gguccucuga cucucuucgg ugacggguau ucuuggugg auaauacgga uuacguuguu         60
auugcuuaag aauacgcgua gucgaggaga guaccagcgg ca                          102

<210> SEQ ID NO 24
<211> LENGTH: 81
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000101
<309> DATABASE ENTRY DATE: 2018-10-01
<313> RELEVANT RESIDUES IN SEQ ID NO: (13)..(36)

<400> SEQUENCE: 24
cccauuggca uaaacccgua gauccgaucu uguggugaag uggaccgcac aagcucgcuu         60
cuaugggucu gugucagugu g                                                  81

<210> SEQ ID NO 25
<211> LENGTH: 976
<212> TYPE: DNA
<213> ORGANISM: Homo sapiens
<300> PUBLICATION INFORMATION:
<301> AUTHORS: Ho, Y.S. and Crapo, J.D.
<302> TITLE: Isolation and characterization of complementary DNAs
       encoding...
<303> JOURNAL: FEBS Lett.
<304> VOLUME: 229
<305> ISSUE: 2
<306> PAGES: 256-260
<307> DATE: 1988-03-14
<308> DATABASE ACCESSION NUMBER: geneBank/M36693
```

<309> DATABASE ENTRY DATE: 1993-08-03
<313> RELEVANT RESIDUES IN SEQ ID NO: (1)..(976)

<400> SEQUENCE: 25

| | | | | | |
|---|---|---|---|---|---|
| gcgggcggcg | caggagcggc | actcgtggct | gtggtggctt | cggcagcggc | ttcagcagat | 60 |
| cggcggcatc | agcggtagca | ccagcactag | cagcatgttg | agccgggcag | tgtgcggcac | 120 |
| cagcaggcag | ctggctccgg | ctttggggta | tctgggctcc | aggcagaagc | acagcctccc | 180 |
| cgacctgccc | tacgactacg | cgccctggaa | acctcacatc | aacgcgcaga | tcatgcagct | 240 |
| gcaccacagc | aagcaccacg | cggcctacgt | gaacaacctg | aacgtcaccg | aggagaagta | 300 |
| ccaggaggcg | ttggccaagg | gagatgttac | agcccagaca | gctcttcagc | ctgcactgaa | 360 |
| gttcaatggt | ggtggtcata | tcaatcatag | cattttctgg | acaaacctca | gccctaacgg | 420 |
| tggtggagaa | cccaaagggg | agttgctgga | agccatcaaa | cgtgactttg | gttcctttga | 480 |
| caagtttaag | gagaagctga | cggctgcatc | tgttggtgtc | caaggctcag | gttggggttg | 540 |
| gcttggtttc | aataaggaac | ggggacactt | acaaattgct | gcttgtccaa | atcaggatcc | 600 |
| actgcaagga | caacaggcc | ttattccact | gctggggatt | gatgtgtggg | agcacgctta | 660 |
| ctaccttcag | tataaaaatg | tcaggcctga | ttatctaaaa | gctatttgga | atgtaatcaa | 720 |
| ctgggagaat | gtaactgaaa | gatacatggc | ttgcaaaaag | taaaccacga | tcgttatgct | 780 |
| gagtatgtta | agctctttat | gactgttttt | gtagtggtat | agagtactgc | agaatacagt | 840 |
| aagctgctct | attgtagcat | ttcttgatgt | tgcttagtca | cttatttcat | aaacaactta | 900 |
| atgttctgaa | taatttctta | ctaaacattt | tgttattggg | caagtgattg | aaaatagtaa | 960 |
| atgctttgtg | tgattg | | | | | 976 |

<210> SEQ ID NO 26
<211> LENGTH: 1748
<212> TYPE: DNA
<213> ORGANISM: Homo sapiens
<300> PUBLICATION INFORMATION:
<301> AUTHORS: Mammalian Gene Collection Program Team
<302> TITLE: Generation and initial analysis of more than 15,000 full-
       length..
<303> JOURNAL: Proc. Natl. Acad. Sci. U.S.A
<304> VOLUME: 99
<305> ISSUE: 26
<306> PAGES: 16899-16903
<307> DATE: 2002-12-11
<308> DATABASE ACCESSION NUMBER: genBank/BC069244
<309> DATABASE ENTRY DATE: 2006-07-15
<313> RELEVANT RESIDUES IN SEQ ID NO: (1)..(1748)

<400> SEQUENCE: 26

| | | | | | |
|---|---|---|---|---|---|
| gtgaggctgc | gcttgcccgg | ggcccgcgcc | ccctacccc | ggggaccgcc | cccgggccgc | 60 |
| ccgccccact | tggcgcgcca | cttccgcgtg | catggccctg | ctgccccgag | ccctgagcgc | 120 |
| cggcgcggga | ccgagctggc | ggcgggcggc | gcgcgccttc | cgaggcttcc | tgctgcttct | 180 |
| gcccgagccc | gcgccctca | cgcgcgccct | ctcccgtgcc | atggcctgca | ggcaggagcc | 240 |
| gcagccgcag | ggcccgccgc | ccgctgctgg | cgccgtggcc | tcctatgact | acctggtgat | 300 |
| cggggcggc | tcgggcgggc | tggccagcgc | gcgcagggcg | gccgagctgg | gtgccagggc | 360 |
| cgccgtggtg | gagagccaca | agctgggtgg | cacttgcgtg | aatgttggat | gtgtacccaa | 420 |
| aaaggtaatg | tggaacacag | ctgtccactc | tgaattcatg | catgatcatg | ctgattatgg | 480 |
| cttttccaagt | tgtgagggta | aattcaattg | gcgtgttatt | aaggaaaagc | gggatgccta | 540 |
| tgtgagccgc | ctgaatgcca | tctatcaaaa | caatctcacc | aagtcccata | tagaaatcat | 600 |

```
ccgtggccat gcagccttca cgagtgatcc caagcccaca atagaggtca gtgggaaaaa      660
gtacaccgcc ccacacatcc tgatcgccac aggtggtatg ccctccaccc ctcatgagag      720
ccagatcccc ggtgccagct taggaataac cagcgatgga ttttttcagc tggaagaatt      780
gcccggccgc agcgtcattg ttggtgcagg ttacattgct gtggagatgg cagggatcct      840
gtcagccctg ggttctaaga catcactgat gatacggcat gataaggtac ttagaagttt      900
tgattcaatg atcagcacca actgcacgga ggagctggag aacgctggcg tggaggtgct      960
gaagttctcc caggtcaagg aggttaaaaa gactttgtcg ggcttggaag tcagcatggt     1020
tactgcagtt cccggtaggc taccagtcat gaccatgatt ccagatgttg actgcctgct     1080
ctgggccatt gggcgggtcc cgaataccaa ggacctgagt ttaaacaaac tgggattca      1140 aaccgatgac aagggtcata tcatcgtaga cgaattccag ataccaacg tcaaaggcat      1200 ctatgcagtt ggggatgtat gtggaaaagc tcttcttact ccagttgcaa tagctgctgg     1260
ccgaaaactt gcccatcgac tttttgaata taaggaagat tccaaattag attataacaa     1320
catcccaact gtggtcttca gccaccccc tattgggaca gtgggactca cggaagatga     1380
agccattcat aaatatggaa tagaaaatgt gaagacctat tcaacgagct ttaccccgat     1440
gtatcacgca gttaccaaaa ggaaaacaaa atgtgtgatg aaaatggtct gtgctaacaa     1500
ggaagaaaag gtggttggga tccatatgca gggacttggg tgtgatgaaa tgctgcaggg     1560
ttttgctgtt gcagtgaaga tgggagcaac gaaggcagac tttgacaaca cagtcgccat     1620
tcaccctacc tcttcagaag agctggtcac acttcgttga gaaccaggag acacgtgtgg     1680
cgggcagtgg gacccataga tcttctgaaa tgaaacaaat aatcacattg aaaaaaaaaa     1740
aaaaaaaa                                                              1748
```

<210> SEQ ID NO 27
<211> LENGTH: 1805
<212> TYPE: DNA
<213> ORGANISM: Homo sapiens
<300> PUBLICATION INFORMATION:
<301> AUTHORS: Matsuya M, Sasaki H, Aoto H, Mitaka T, Nagura K, Ohba T,
       Ishino M, Takahashi S, Suzuki R and Sasaki T.
<302> TITLE: Cell adhesion kinase beta forms a complex with a new
       member, Hic-5,
<303> JOURNAL: J. Biol. Chem.
<304> VOLUME: 273
<305> ISSUE: 2
<306> PAGES: 1003-1014
<307> DATE: 1998-01-09
<308> DATABASE ACCESSION NUMBER: genBank/NM_001042454
<309> DATABASE ENTRY DATE: 2020-02-29
<300> PUBLICATION INFORMATION:
<308> DATABASE ACCESSION NUMBER: OMIM.org: 602353
<309> DATABASE ENTRY DATE: 2024-05-02
<313> RELEVANT RESIDUES IN SEQ ID NO: (1)..(1805)

<400> SEQUENCE: 27

```
gccctgttcg ccccgcgcca ccggcccgcg cccgccatg gaggacctgg atgccctgct       60
ctctgacctg gagactacca cctcgcacat gccaaggtca ggggctccca agagcgccc      120 tgcggagcct ctcacccctc ccccatccta tggccaccag ccacagacag gtctgggga     180 gtcttcagga gcctcggggg acaaggacca cctgtacagc acggtatgca agcctcggtc      240
cccaaagcct gcagccccgg cggcccctcc attctcctct tccagcggtg tcttgggtac      300
cgggctctgt gagctagatc ggttgcttca ggaacttaat gccactcagt tcaacatcac      360
agatgaaatc atgtctcagt tcccatctag caaggtggct tcaggagagc agaaggagga      420
ccagtctgaa gataagaaaa gacccagcct cccttccagc ccgtctcctg gcctcccaaa      480
```

```
ggcttctgcc acctcagcca ctctggagct ggatagactg atggcctcac tctctgactt    540
ccgcgttcaa aaccatcttc cagcctctgg gccaactcag ccaccggtgg tgagctccac    600
aaatgagggc tccccatccc caccagagcc gactggcaag ggcagcctag acaccatgct    660
ggggctgctg cagtccgacc tcagccgccg gggtgttccc acccaggcca aaggcctctg    720
tggctcctgc aataaaccta ttgctgggca agtggtgacg gctctgggcc gcgcctggca    780
ccccgagcac ttcgtttgcg gaggctgttc caccgccctg ggaggcagca gcttcttcga    840
gaaggatgga gccccttct gccccgagtg ctactttgag cgcttctcgc caagatgtgg    900
cttctgcaac cagcccatcc gacacaagat ggtgaccgcc ttgggcactc actggcaccc    960
agagcatttc tgctgcgtca gttgcgggga gcccttcgga gatgagggtt ccacgagcg    1020 cgagggccgc ccctactgcc gccgggactt cctgcagctg ttcgccccgc gctgccaggg    1080
ctgccagggc cccatcctgg ataactacat ctcggcgctc agcgcgctct ggcacccgga    1140
ctgtttcgtc tgcagggaat gcttcgcgcc cttctcggga ggcagttttt tcgagcacga    1200
gggccgcccg ttgtgcgaga accacttcca cgcacgacgc ggctcgctgt gcgccacgtg    1260
tggcctccct gtgaccggcc gctgcgtgtc ggccctgggt cgccgcttcc acccggacca    1320
cttcacatgc accttctgcc tgcgcccgct caccaagggg tccttccagg agcgcgccgg    1380
caagccctac tgccagccct gcttcctgaa gctcttcggc tgacagcccg ctcggctcgc    1440
cctctccccc ggaggccgcg ccctcccgga aaagccgggt cctccagacc ccgaggcctt    1500
gctctcagag cgggaggccc cacccactgg agagccccgc ccctaaggta ctatgagtcc    1560 tcagggtca agttcagaaa cggcccagcc agacctaaac ccacacgccc acaaagtgga    1620
ttgcacacag acaagaactc ccgtgcgggc ctccactcta ttcccaccct tgagggagcc    1680
cccttactgg gggagggtcc ttgcaattcc agcgaatcgg aggccaggcc aggacgtcct    1740
tgctccctgc accctcactg ttctgtgcac ttttttctacc tacataaaca cacgcattcc    1800
acctc                                                                1805
```

<210> SEQ ID NO 28
<211> LENGTH: 21
<212> TYPE: RNA
<213> ORGANISM: Homo sapiens
<300> PUBLICATION INFORMATION:
<301> AUTHORS: Shi, Yan et al.
<302> TITLE: MicroRNA-219a-5p Suppresses Intestinal Inflammation...
<303> JOURNAL: Mucosal Immunol
<304> VOLUME: 13
<305> ISSUE: 2
<306> PAGES: 303-312
<307> DATE: 2019-10-18
<308> DATABASE ACCESSION NUMBER: www.mirbase.org/MIMAT0000276
<309> DATABASE ENTRY DATE: 2018-10-01
<313> RELEVANT RESIDUES IN SEQ ID NO: (1)..(21)

<400> SEQUENCE: 28
ugauugucca aacgcaauuc u                                               21

<210> SEQ ID NO 29
<211> LENGTH: 99
<212> TYPE: RNA
<213> ORGANISM: Homo sapiens
<300> PUBLICATION INFORMATION:
<301> AUTHORS: Landgraf, P. et al.
<302> TITLE: A mammalian microRNA expression atlas...
<303> JOURNAL: Cell
<304> VOLUME: 129
<305> ISSUE: 7

```
<306> PAGES: 1401-1414
<307> DATE: 2007-06-29
<308> DATABASE ACCESSION NUMBER: www.mirbase.org/MI0000477
<309> DATABASE ENTRY DATE: 2018-10-01
<313> RELEVANT RESIDUES IN SEQ ID NO: (21)..(43)

<400> SEQUENCE: 29
ccgaugugua uccucagcuu ugagaacuga auuccauggg uugugucagu gucagaccuc      60
ugaaauucag uucuucagcu gggauaucuc ugucaucgu                             99

<210> SEQ ID NO 30
<211> LENGTH: 85
<212> TYPE: DNA
<213> ORGANISM: Homo sapiens
<300> PUBLICATION INFORMATION:
<301> AUTHORS: Landgraf P., et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0000074
<309> DATABASE ENTRY DATE: 2018-10-01
<313> RELEVANT RESIDUES IN SEQ ID NO: (54)..(76)

<400> SEQUENCE: 30
cuguucuaug guuaguuuug cagguuugca uccagcugug ugauauucug cugugcaaau      60
ccaugcaaaa cugacugugg uagug                                            85

<210> SEQ ID NO 31
<211> LENGTH: 22
<212> TYPE: DNA
<213> ORGANISM: Homo sapiens
<300> PUBLICATION INFORMATION:
<301> AUTHORS: Landgraf P., et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER:
      www.mirbase.org/www.mirbase.org/www.mirbase.org/MIMAT0003258
<309> DATABASE ENTRY DATE: 2018-10-01
<313> RELEVANT RESIDUES IN SEQ ID NO: (1)..(22)

<400> SEQUENCE: 31
gagcuuauuc auaaaagugc ag                                               22

<210> SEQ ID NO 32
<211> LENGTH: 81
<212> TYPE: DNA
<213> ORGANISM: Homo sapiens
<300> PUBLICATION INFORMATION:
<301> AUTHORS: Landgraf P. et al.
<302> TITLE: A mammalian microRNA expression atlas...
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MI0003135
<309> DATABASE ENTRY DATE: 2018-10-01
<313> RELEVANT RESIDUES IN SEQ ID NO: (14)..(36)

<400> SEQUENCE: 32
gguaccugaa aagaaguugc ccauguuauu uucgcuuuau augugacgaa acaaacaugg      60
ugcacuucuu uuucgguauc a                                                81
```

<210> SEQ ID NO 33

<400> SEQUENCE: 33

000

<210> SEQ ID NO 34
<211> LENGTH: 23
<212> TYPE: DNA
<213> ORGANISM: Epstein Barr virus
<300> PUBLICATION INFORMATION:
<301> AUTHORS: Landgraf P. et al.
<302> TITLE: A mammalian microRNA expression atlas based on small RNA
      library sequencing
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MIMAT0003420
<309> DATABASE ENTRY DATE: 2014-05-30
<313> RELEVANT RESIDUES IN SEQ ID NO: (1)..(23)
<300> PUBLICATION INFORMATION:
<301> AUTHORS: Landgraf P. et al.
<302> TITLE: A mammalian microRNA expression atlas..
<303> JOURNAL: Cell
<304> VOLUME: 129
<305> ISSUE: 7
<306> PAGES: 1401-1414
<307> DATE: 2007-06-29
<308> DATABASE ACCESSION NUMBER: www.mirbase.org/MIMAT0003422
<309> DATABASE ENTRY DATE: 2014-05-30
<313> RELEVANT RESIDUES IN SEQ ID NO: (1)..(23)

<400> SEQUENCE: 34
uacauaacca uggaguuggc ugu                                             23

<210> SEQ ID NO 35
<211> LENGTH: 300
<212> TYPE: PRT
<213> ORGANISM: Human herpes virus 1
<300> PUBLICATION INFORMATION:
<301> AUTHORS: G. D. Elliott and D. M. Meredith
<302> TITLE: The Herpes Simplex Virus Type 1 Tegument Protein VP22...
<303> JOURNAL: J Gen Virol
<304> VOLUME: 73
<305> ISSUE: 3
<306> PAGES: 723-6
<307> DATE: 1992-03-01
<308> DATABASE ACCESSION NUMBER: UNIprot/P10233-1
<309> DATABASE ENTRY DATE: 1989-07-01
<313> RELEVANT RESIDUES IN SEQ ID NO: (1)..(300)

<400> SEQUENCE: 35

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Pro Ala Gly Ser Gly Gly Ala Gly

```
                    100                 105                 110
Arg Thr Pro Thr Thr Ala Pro Arg Ala Pro Arg Thr Gln Arg Val Ala
                115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
                180                 185                 190

Val Ala Gly Phe Asn Lys Arg Val Phe Cys Ala Ala Val Gly Arg Leu
                195                 200                 205

Ala Ala Met His Ala Arg Met Ala Ala Val Gln Leu Trp Asp Met Ser
                210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
                260                 265                 270

Thr Arg Gly Arg Ser Ala Ala Ser Arg Pro Thr Glu Arg Pro Arg Ala
                275                 280                 285

Pro Ala Arg Ser Ala Ser Arg Pro Arg Arg Pro Val
                290                 295                 300

<210> SEQ ID NO 36
<211> LENGTH: 561
<212> TYPE: PRT
<213> ORGANISM: Human Herpes Virus 5
<300> PUBLICATION INFORMATION:
<301> AUTHORS: Abate D.A., Watanabe S., and Mocarski E.S.
<302> TITLE: Major human cytomegalovirus structural protein pp65...
<303> JOURNAL: J Gen Virol
<304> VOLUME: 78
<305> ISSUE: 20
<306> PAGES: 10995-11006
<307> DATE: 2004-10-01
<308> DATABASE ACCESSION NUMBER: UNIprot/P06725
<309> DATABASE ENTRY DATE: 1989-07-01
<313> RELEVANT RESIDUES IN SEQ ID NO: (1)..(561)

<400> SEQUENCE: 36

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Gly Ile His Val
            35                  40                  45

Arg Val Ser Gln Pro Ser Leu Ile Leu Val Ser Gln Tyr Thr Pro Asp
        50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
```

-continued

```
                115                 120                 125
His His Tyr Pro Ser Ala Ala Glu Arg Lys His Arg His Leu Pro Val
            130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
                195                 200                 205

Glu Asn Thr Arg Ala Thr Lys Met Gln Val Ile Gly Asp Gln Tyr Val
            210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
                275                 280                 285

His Ile Met Leu Asp Val Ala Phe Thr Ser His Glu His Phe Gly Leu
            290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
                355                 360                 365

Phe Thr Ser Gln Tyr Arg Ile Gln Gly Lys Leu Glu Tyr Arg His Thr
            370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Thr Ser
            420                 425                 430

Ala Gly Arg Lys Arg Lys Ser Ala Ser Ser Ala Thr Ala Cys Thr Ser
            435                 440                 445

Gly Val Met Thr Arg Gly Arg Leu Lys Ala Glu Ser Thr Val Ala Pro
            450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
            515                 520                 525

Gly Val Trp Gln Pro Ala Ala Gln Pro Lys Arg Arg Arg His Arg Gln
            530                 535                 540
```

-continued

```
Asp Ala Leu Pro Gly Pro Cys Ile Ala Ser Thr Pro Lys Lys His Arg
545                 550                 555                 560

Gly

<210> SEQ ID NO 37
<211> LENGTH: 2096
<212> TYPE: PRT
<213> ORGANISM: Human Herpes Virus 5
<300> PUBLICATION INFORMATION:
<301> AUTHORS: Aucoin D.P., Smith G.B., Meiering C.D., Mocarski E.S.
<302> TITLE: Betaherpesvirus-conserved cytomegalovirus tegument protein
      ppUL32 (pp150)
<303> JOURNAL: J Gen Virol
<304> VOLUME: 80
<305> ISSUE: 16
<306> PAGES: 8199-8210
<307> DATE: 2006-08-01
<308> DATABASE ACCESSION NUMBER: UNIprot/P08318
<309> DATABASE ENTRY DATE: 1988-08-01
<313> RELEVANT RESIDUES IN SEQ ID NO: (1)..(2096)

<400> SEQUENCE: 37

Met Ser Leu Gln Phe Ile Gly Leu Gln Arg Arg Asp Val Val Ala Leu
1               5                   10                  15

Val Asn Phe Leu Arg His Leu Thr Gln Lys Pro Asp Val Asp Leu Glu
                20                  25                  30

Ala His Pro Lys Ile Leu Lys Lys Cys Gly Glu Lys Arg Leu His Arg
            35                  40                  45

Arg Thr Val Leu Phe Asn Glu Leu Met Leu Trp Leu Gly Tyr Tyr Arg
        50                  55                  60

Glu Leu Arg Phe His Asn Pro Asp Leu Ser Ser Val Leu Glu Glu Phe
65                  70                  75                  80

Glu Val Arg Cys Val Ala Val Ala Arg Arg Gly Tyr Thr Tyr Pro Phe
                85                  90                  95

Gly Asp Arg Gly Lys Ala Arg Asp His Leu Ala Val Leu Asp Arg Thr
            100                 105                 110

Glu Phe Asp Thr Asp Val Arg His Asp Ala Glu Ile Val Glu Arg Ala
        115                 120                 125

Leu Val Ser Ala Val Ile Leu Ala Lys Met Ser Val Arg Glu Thr Leu
130                 135                 140

Val Thr Ala Ile Gly Gln Thr Glu Pro Ile Ala Phe Val His Leu Lys
145                 150                 155                 160

Asp Thr Glu Val Gln Arg Ile Glu Glu Asn Leu Glu Gly Val Arg Arg
                165                 170                 175

Asn Met Phe Cys Val Lys Pro Leu Asp Leu Asn Leu Asp Arg His Ala
            180                 185                 190

Asn Thr Ala Leu Val Asn Ala Val Asn Lys Leu Val Tyr Thr Gly Arg
        195                 200                 205

Leu Ile Met Asn Val Arg Arg Ser Trp Glu Glu Leu Glu Arg Lys Cys
210                 215                 220

Leu Ala Arg Ile Gln Glu Arg Cys Lys Leu Leu Val Lys Glu Leu Arg
225                 230                 235                 240

Met Cys Leu Ser Phe Asp Ser Asn Tyr Cys Arg Asn Ile Leu Lys His
                245                 250                 255

Ala Val Glu Asn Gly Asp Ser Ala Asp Thr Leu Leu Glu Leu Leu Ile
            260                 265                 270

Glu Asp Phe Asp Ile Tyr Val Asp Ser Phe Pro Gln Ser Ala His Thr
        275                 280                 285
```

Phe Leu Gly Ala Arg Ser Pro Ser Leu Glu Phe Asp Asp Ala Asn
    290                 295                 300

Leu Leu Ser Leu Gly Gly Ser Ala Phe Ser Ser Val Pro Lys Lys
305                 310                 315                 320

His Val Pro Thr Gln Pro Leu Asp Gly Trp Ser Trp Ile Ala Ser Pro
                325                 330                 335

Trp Lys Gly His Lys Pro Phe Arg Phe Glu Ala His Gly Ser Leu Ala
                340                 345                 350

Pro Ala Ala Glu Ala His Ala Ala Arg Ser Ala Ala Val Gly Tyr Tyr
                355                 360                 365

Asp Glu Glu Glu Lys Arg Arg Glu Arg Gln Lys Arg Val Asp Asp Glu
    370                 375                 380

Val Val Gln Arg Glu Lys Gln Gln Leu Lys Ala Trp Glu Glu Arg Gln
385                 390                 395                 400

Gln Asn Leu Gln Gln Arg Gln Gln Gln Pro Pro Pro Ala Arg Lys
                405                 410                 415

Pro Ser Ala Ser Arg Arg Leu Phe Gly Ser Ser Ala Asp Glu Asp Asp
                420                 425                 430

Asp Asp Asp Asp Glu Lys Asn Ile Phe Thr Pro Ile Lys Lys Pro
    435                 440                 445

Gly Thr Ser Gly Lys Gly Ala Ala Ser Gly Gly Val Ser Ser Ile
    450                 455                 460

Phe Ser Gly Leu Leu Ser Ser Gly Ser Gln Lys Pro Thr Ser Gly Pro
465                 470                 475                 480

Leu Asn Ile Pro Gln Gln Gln Gln Arg His Ala Ala Phe Ser Leu Val
                485                 490                 495

Ser Pro Gln Val Thr Lys Ala Ser Pro Gly Arg Val Arg Arg Asp Ser
                500                 505                 510

Ala Trp Asp Val Arg Pro Leu Thr Glu Thr Arg Gly Asp Leu Phe Ser
                515                 520                 525

Gly Asp Glu Asp Ser Asp Ser Ser Asp Gly Tyr Pro Pro Asn Arg Gln
                530                 535                 540

Asp Pro Arg Phe Thr Asp Thr Leu Val Asp Ile Thr Asp Thr Glu Thr
545                 550                 555                 560

Ser Ala Lys Pro Pro Val Thr Thr Ala Tyr Lys Phe Glu Gln Pro Thr
                565                 570                 575

Leu Thr Phe Gly Ala Gly Val Asn Val Pro Ala Gly Ala Gly Ala Ala
                580                 585                 590

Ile Leu Thr Pro Thr Pro Val Asn Pro Ser Thr Ala Pro Ala Pro Ala
                595                 600                 605

Pro Thr Pro Thr Phe Ala Gly Thr Gln Thr Pro Val Asn Gly Asn Ser
                610                 615                 620

Pro Trp Ala Pro Thr Ala Pro Leu Pro Gly Asp Met Asn Pro Ala Asn
625                 630                 635                 640

Trp Pro Arg Glu Arg Ala Trp Ala Leu Lys Asn Pro His Leu Ala Tyr
                645                 650                 655

Asn Pro Phe Arg Met Pro Thr Thr Ser Thr Ala Ser Gln Asn Thr Val
                660                 665                 670

Ser Thr Thr Pro Arg Arg Pro Ser Thr Pro Arg Ala Ala Val Thr Gln
            675                 680                 685

Thr Ala Ser Arg Asp Ala Ala Asp Glu Val Trp Ala Leu Arg Asp Gln
    690                 695                 700

-continued

```
Thr Ala Glu Ser Pro Val Glu Asp Ser Glu Glu Asp Asp Ser
705                 710                 715                 720

Ser Asp Thr Gly Ser Val Val Ser Leu Gly His Thr Thr Pro Ser Ser
                725                 730                 735

Asp Tyr Asn Asn Asp Val Ile Ser Pro Ser Gln Thr Pro Glu Gln
            740                 745                 750

Ser Thr Pro Ser Arg Ile Arg Lys Ala Lys Leu Ser Ser Pro Met Thr
        755                 760                 765

Thr Thr Ser Thr Ser Gln Lys Pro Val Leu Gly Lys Arg Val Ala Thr
    770                 775                 780

Pro His Ala Ser Ala Arg Ala Gln Thr Val Thr Ser Thr Pro Val Gln
785                 790                 795                 800

Gly Arg Leu Glu Lys Gln Val Ser Gly Thr Pro Ser Thr Val Pro Ala
                805                 810                 815

Thr Leu Leu Gln Pro Gln Pro Ala Ser Ser Lys Thr Thr Ser Ser Arg
            820                 825                 830

Asn Val Thr Ser Gly Ala Gly Thr Ser Ser Ala Ser Ser Ala Arg Gln
        835                 840                 845

Pro Ser Ala Ser Ala Ser Val Leu Ser Pro Thr Glu Asp Asp Val Val
    850                 855                 860

Ser Pro Ala Thr Ser Pro Leu Ser Met Leu Ser Ser Ala Ser Pro Ser
865                 870                 875                 880

Pro Ala Lys Ser Ala Pro Pro Ser Pro Val Lys Gly Arg Gly Ser Arg
                885                 890                 895

Val Gly Val Pro Ser Leu Lys Pro Thr Leu Gly Gly Lys Ala Val Val
            900                 905                 910

Gly Arg Pro Pro Ser Val Pro Val Ser Gly Ser Ala Pro Gly Arg Leu
        915                 920                 925

Ser Gly Ser Ser Arg Ala Ala Ser Thr Thr Pro Thr Tyr Pro Ala Val
    930                 935                 940

Thr Thr Val Tyr Pro Pro Ser Ser Thr Ala Lys Ser Ser Val Ser Asn
945                 950                 955                 960

Ala Pro Pro Val Ala Ser Pro Ser Ile Leu Lys Pro Gly Ala Ser Ala
                965                 970                 975

Ala Leu Gln Ser Arg Arg Ser Thr Gly Thr Ala Ala Val Gly Ser Pro
            980                 985                 990

Val Lys Ser Thr Thr Gly Met Lys Thr Val Ala Phe Asp Leu Ser Ser
        995                 1000                1005

Pro Gln Lys Ser Gly Thr Gly Pro Gln Pro Gly Ser Ala Gly Met
    1010                1015                1020

Gly Gly Ala Lys Thr Pro Ser Asp Ala Val Gln Asn Ile Leu Gln
    1025                1030                1035

Lys Ile Glu Lys Ile Lys Asn Thr Glu Glu Met Ser Leu Gln Phe
    1040                1045                1050

Ile Gly Leu Gln Arg Arg Asp Val Val Ala Leu Val Asn Phe Leu
    1055                1060                1065

Arg His Leu Thr Gln Lys Pro Asp Val Asp Leu Glu Ala His Pro
    1070                1075                1080

Lys Ile Leu Lys Lys Cys Gly Glu Lys Arg Leu His Arg Arg Thr
    1085                1090                1095

Val Leu Phe Asn Glu Leu Met Leu Trp Leu Gly Tyr Tyr Arg Glu
    1100                1105                1110

Leu Arg Phe His Asn Pro Asp Leu Ser Ser Val Leu Glu Glu Phe
```

```
                  1115                1120                1125

Glu Val Arg Cys Val Ala Val Ala Arg Arg Gly Tyr Thr Tyr Pro
        1130                1135                1140

Phe Gly Asp Arg Gly Lys Ala Arg Asp His Leu Ala Val Leu Asp
        1145                1150                1155

Arg Thr Glu Phe Asp Thr Asp Val Arg His Asp Ala Glu Ile Val
        1160                1165                1170

Glu Arg Ala Leu Val Ser Ala Val Ile Leu Ala Lys Met Ser Val
        1175                1180                1185

Arg Glu Thr Leu Val Thr Ala Ile Gly Gln Thr Glu Pro Ile Ala
        1190                1195                1200

Phe Val His Leu Lys Asp Thr Glu Val Gln Arg Ile Glu Glu Asn
        1205                1210                1215

Leu Glu Gly Val Arg Arg Asn Met Phe Cys Val Lys Pro Leu Asp
        1220                1225                1230

Leu Asn Leu Asp Arg His Ala Asn Thr Ala Leu Val Asn Ala Val
        1235                1240                1245

Asn Lys Leu Val Tyr Thr Gly Arg Leu Ile Met Asn Val Arg Arg
        1250                1255                1260

Ser Trp Glu Glu Leu Glu Arg Lys Cys Leu Ala Arg Ile Gln Glu
        1265                1270                1275

Arg Cys Lys Leu Leu Val Lys Glu Leu Arg Met Cys Leu Ser Phe
        1280                1285                1290

Asp Ser Asn Tyr Cys Arg Asn Ile Leu Lys His Ala Val Glu Asn
        1295                1300                1305

Gly Asp Ser Ala Asp Thr Leu Leu Glu Leu Leu Ile Glu Asp Phe
        1310                1315                1320

Asp Ile Tyr Val Asp Ser Phe Pro Gln Ser Ala His Thr Phe Leu
        1325                1330                1335

Gly Ala Arg Ser Pro Ser Leu Glu Phe Asp Asp Asp Ala Asn Leu
        1340                1345                1350

Leu Ser Leu Gly Gly Gly Ser Ala Phe Ser Ser Val Pro Lys Lys
        1355                1360                1365

His Val Pro Thr Gln Pro Leu Asp Gly Trp Ser Trp Ile Ala Ser
        1370                1375                1380

Pro Trp Lys Gly His Lys Pro Phe Arg Phe Glu Ala His Gly Ser
        1385                1390                1395

Leu Ala Pro Ala Ala Glu Ala His Ala Ala Arg Ser Ala Ala Val
        1400                1405                1410

Gly Tyr Tyr Asp Glu Glu Glu Lys Arg Arg Glu Arg Gln Lys Arg
        1415                1420                1425

Val Asp Asp Glu Val Val Gln Arg Glu Lys Gln Gln Leu Lys Ala
        1430                1435                1440

Trp Glu Glu Arg Gln Gln Asn Leu Gln Gln Arg Gln Gln Gln Pro
        1445                1450                1455

Pro Pro Pro Ala Arg Lys Pro Ser Ala Ser Arg Arg Leu Phe Gly
        1460                1465                1470

Ser Ser Ala Asp Glu Asp Asp Asp Asp Asp Asp Glu Lys Asn
        1475                1480                1485

Ile Phe Thr Pro Ile Lys Lys Pro Gly Thr Ser Gly Lys Gly Ala
        1490                1495                1500

Ala Ser Gly Gly Gly Val Ser Ser Ile Phe Ser Gly Leu Leu Ser
        1505                1510                1515
```

```
Ser Gly Ser Gln Lys Pro Thr Ser Gly Pro Leu Asn Ile Pro Gln
1520                1525                1530

Gln Gln Gln Arg His Ala Ala Phe Ser Leu Val Ser Pro Gln Val
1535                1540                1545

Thr Lys Ala Ser Pro Gly Arg Val Arg Arg Asp Ser Ala Trp Asp
1550                1555                1560

Val Arg Pro Leu Thr Glu Thr Arg Gly Asp Leu Phe Ser Gly Asp
1565                1570                1575

Glu Asp Ser Asp Ser Ser Asp Gly Tyr Pro Pro Asn Arg Gln Asp
1580                1585                1590

Pro Arg Phe Thr Asp Thr Leu Val Asp Ile Thr Asp Thr Glu Thr
1595                1600                1605

Ser Ala Lys Pro Pro Val Thr Thr Ala Tyr Lys Phe Glu Gln Pro
1610                1615                1620

Thr Leu Thr Phe Gly Ala Gly Val Asn Val Pro Ala Gly Ala Gly
1625                1630                1635

Ala Ala Ile Leu Thr Pro Thr Pro Val Asn Pro Ser Thr Ala Pro
1640                1645                1650

Ala Pro Ala Pro Thr Pro Thr Phe Ala Gly Thr Gln Thr Pro Val
1655                1660                1665

Asn Gly Asn Ser Pro Trp Ala Pro Thr Ala Pro Leu Pro Gly Asp
1670                1675                1680

Met Asn Pro Ala Asn Trp Pro Arg Glu Arg Ala Trp Ala Leu Lys
1685                1690                1695

Asn Pro His Leu Ala Tyr Asn Pro Phe Arg Met Pro Thr Thr Ser
1700                1705                1710

Thr Ala Ser Gln Asn Thr Val Ser Thr Thr Pro Arg Arg Pro Ser
1715                1720                1725

Thr Pro Arg Ala Ala Val Thr Gln Thr Ala Ser Arg Asp Ala Ala
1730                1735                1740

Asp Glu Val Trp Ala Leu Arg Asp Gln Thr Ala Glu Ser Pro Val
1745                1750                1755

Glu Asp Ser Glu Glu Glu Asp Asp Asp Ser Ser Asp Thr Gly Ser
1760                1765                1770

Val Val Ser Leu Gly His Thr Thr Pro Ser Ser Asp Tyr Asn Asn
1775                1780                1785

Asp Val Ile Ser Pro Pro Ser Gln Thr Pro Glu Gln Ser Thr Pro
1790                1795                1800

Ser Arg Ile Arg Lys Ala Lys Leu Ser Ser Pro Met Thr Thr Thr
1805                1810                1815

Ser Thr Ser Gln Lys Pro Val Leu Gly Lys Arg Val Ala Thr Pro
1820                1825                1830

His Ala Ser Ala Arg Ala Gln Thr Val Thr Ser Thr Pro Val Gln
1835                1840                1845

Gly Arg Leu Glu Lys Gln Val Ser Gly Thr Pro Ser Thr Val Pro
1850                1855                1860

Ala Thr Leu Leu Gln Pro Gln Pro Ala Ser Ser Lys Thr Thr Ser
1865                1870                1875

Ser Arg Asn Val Thr Ser Gly Ala Gly Thr Ser Ser Ala Ser Ser
1880                1885                1890

Ala Arg Gln Pro Ser Ala Ser Ala Ser Val Leu Ser Pro Thr Glu
1895                1900                1905
```

```
Asp Asp  Val Val Ser Pro Ala  Thr Ser Pro Leu Ser  Met Leu Ser
    1910             1915             1920

Ser Ala  Ser Pro Ser Pro Ala  Lys Ser Ala Pro Pro  Ser Pro Val
    1925             1930             1935

Lys Gly  Arg Gly Ser Arg Val  Gly Val Pro Ser Leu  Lys Pro Thr
    1940             1945             1950

Leu Gly  Gly Lys Ala Val Val  Gly Arg Pro Pro Ser  Val Pro Val
    1955             1960             1965

Ser Gly  Ser Ala Pro Gly Arg  Leu Ser Gly Ser Ser  Arg Ala Ala
    1970             1975             1980

Ser Thr  Thr Pro Thr Tyr Pro  Ala Val Thr Thr Val  Tyr Pro Pro
    1985             1990             1995

Ser Ser  Thr Ala Lys Ser Ser  Val Ser Asn Ala Pro  Pro Val Ala
    2000             2005             2010

Ser Pro  Ser Ile Leu Lys Pro  Gly Ala Ser Ala Ala  Leu Gln Ser
    2015             2020             2025

Arg Arg  Ser Thr Gly Thr Ala  Ala Val Gly Ser Pro  Val Lys Ser
    2030             2035             2040

Thr Thr  Gly Met Lys Thr Val  Ala Phe Asp Leu Ser  Ser Pro Gln
    2045             2050             2055

Lys Ser  Gly Thr Gly Pro Gln  Pro Gly Ser Ala Gly  Met Gly Gly
    2060             2065             2070

Ala Lys  Thr Pro Ser Asp Ala  Val Gln Asn Ile Leu  Gln Lys Ile
    2075             2080             2085

Glu Lys  Ile Lys Asn Thr Glu  Glu
    2090             2095
```